(12) United States Patent
Sweeney, II et al.

(10) Patent No.: US 11,141,229 B2
(45) Date of Patent: Oct. 12, 2021

(54) DYNAMIC FEEDBACK END EFFECTOR

(71) Applicant: Rubicon Spine LLC, Sarasota, FL (US)

(72) Inventors: Thomas Sweeney, II, Sarasota, FL (US); John D. Kuczynski, Sarasota, FL (US)

(73) Assignee: Rubicon Spine LLC, Sarasota, FL (US)

( * ) Notice: Subject to any disclaimer, the term of this patent is extended or adjusted under 35 U.S.C. 154(b) by 228 days.

(21) Appl. No.: 16/572,290

(22) Filed: Sep. 16, 2019

(65) Prior Publication Data

US 2020/0155242 A1   May 21, 2020

Related U.S. Application Data

(63) Continuation-in-part of application No. 15/612,290, filed on Jun. 2, 2017, now Pat. No. 10,413,371.

(60) Provisional application No. 62/392,523, filed on Jun. 3, 2016.

(51) Int. Cl.
*A61B 34/30* (2016.01)
*A61B 34/00* (2016.01)

(52) U.S. Cl.
CPC .............. *A61B 34/30* (2016.02); *A61B 34/71* (2016.02)

(58) Field of Classification Search
CPC ......... A61B 34/32; A61B 34/30; A61B 34/71; A61B 46/10; A61B 17/1671; A61B 17/7082; A61B 17/7083; A61B 19/20; A61B 19/5244; A61B 19/5225; A61B 19/2203; A61B 19/50; A61B 2090/031; A61B 2090/064; A61B 2090/066; A61B 2917/00026; A61B 2917/00477; A61B 2019/207; A61B 2019/5255; A61B 2019/5236; A61B 2019/5238; A61B 2019/524; A61B 2019/2211
See application file for complete search history.

(56) References Cited

U.S. PATENT DOCUMENTS

| | | | |
|---|---|---|---|
| 8,100,947 B2 | 1/2012 | Ensign et al. |
| 8,100,948 B2 | 1/2012 | Ensign et al. |
| 9,232,965 B2 | 1/2016 | Hawkes |
| 9,283,048 B2 | 3/2016 | Kostrzewski et al. |
| 2006/0147129 A1 | 7/2006 | Miller |
| 2008/0015597 A1 | 1/2008 | Whipple |
| 2008/0058812 A1 | 3/2008 | Zehnder |
| 2008/0147129 A1 | 6/2008 | Biedermann et al. |
| 2008/0243185 A1 | 10/2008 | Felix et al. |
| 2008/0243193 A1 | 10/2008 | Ensign et al. |

(Continued)

*Primary Examiner* — Pedro Philogene
(74) *Attorney, Agent, or Firm* — Kim IP Law Group LLC

(57) ABSTRACT

An end effector of a robotic surgery system that includes a fixed plate for attaching an end of a robotic arm, a shaft extending from the fixed plate, a sliding plate moveable relative to the fixed plate along an axial direction of the shaft, a hub assembly mounted to the sliding plate and operatively engaged with the shaft. The hub assembly includes an idler hub, and an inner bearing moveable relative to the idler hub and operatively engaged with the shaft, whereby rotation of the inner bearing moves the sliding plate along the axial direction of the shaft. The end effector further includes a pulley that includes a driven wheel connected to the inner bearing operatively engaged with a motor, whereby rotation of the driven wheel drives rotation of the inner bearing.

20 Claims, 20 Drawing Sheets

(56) References Cited

U.S. PATENT DOCUMENTS

| | | |
|---|---|---|
| 2009/0105770 A1 | 4/2009 | Berrevoets et al. |
| 2010/0152785 A1 | 6/2010 | Forton et al. |
| 2012/0265051 A1* | 10/2012 | Fischer .................. A61B 90/11 600/411 |
| 2013/0172937 A1 | 7/2013 | Davenport et al. |
| 2014/0214097 A1 | 7/2014 | Jackson et al. |
| 2015/0305817 A1 | 10/2015 | Kostrzewski |
| 2016/0038204 A1 | 2/2016 | Biedermann et al. |
| 2016/0151120 A1* | 6/2016 | Kostrzewski .......... A61B 90/50 606/130 |
| 2018/0303519 A1 | 10/2018 | Liu et al. |

* cited by examiner

DYNAMIC FEEDBACK END EFFECTOR

FIELD OF INVENTION

The present invention is in the field of robotic surgeries.

CROSS-REFERENCE TO RELATED APPLICATIONS

This application is a continuation-in-part application of U.S. application Ser. No. 15/612,290, filed Jun. 2, 2017, which claims the benefit of U.S. Provisional Patent Application 62/392,523 filed on Jun. 3, 2016, the contents of each of which are hereby incorporated by reference.

BACKGROUND

Industrial robots have been in use since the 1960's, with the automobile industry being the first to apply such technology. Later, other industries applied robots to their manufacturing processes, increasing productivity, as well as accuracy and repeatability. Robots have been used for orthopedic surgery since the early 1990's. The ROBODOC system was the first to do the bone resections for joint replacement using a robot with a mill that profiled he surfaces of the bone in the proper shape and orientation to receive prosthesis. Laker MAKO Surgical produced the RIO system which is used to perform partial knee and total hip replacement surgery. Mazor Robotics currently makes the Renaissance robotic surgery system to assist in the performance of spinal surgeries.

In the field of Robotics, the end effector is the device at the end of the robotic arm that interacts with the work environment of the robotic system. Some examples of end effectors in industrial robotics are grippers, designed to grab and release an item when the robot is used for pick and place operations, an arc welder, when the robot is used for welding operations, or a spray paint nozzle, when the robot is used for painting operations. In the case of the ROB ODOC robot, the end effector is a pistol-shaped pneumatic drill equipped with a milling cutter, used for cutting the proximal tibia.

Robots are currently utilized in spine surgery to provide axial alignment to the pedicles and to control the depth of the tool or implant being inserted into the pedicle. The software utilizes CT data from the patient to help the surgeon plan a surgery in a virtual environment. During the operation, a positioning rack may be attached to the patient's spine and acts as a fixed base. Anteroposterior (AP) and Medio-Lateral (ML) X-rays are used to create a 3-dimensional (3D) alignment of the patient that matches the patient's CT data and used to create a coordinate system (for example, X, Y, X, Yaw, Pitch and Roll) for the robot to use.

SUMMARY

An end effector described herein may be applied to an industrial robotics system that may be used to perform spinal reconstructive surgery. The end effector may have specific capabilities and features that may allow a robotic system to perform surgical steps more effectively and safely. When a robot is performing surgical steps, the end effector may act as the "hands" of a surgeon. The end effector may hold the instrument. The end effector may maneuver the instrument, like a surgeon would, with precision and the appropriate amount of force. The end effector may also detect problems, like the surgeon's hands would, for example, if too much force is encountered during a surgical step. The end effector may also control the force applied to a cutting tool and adjust the feed rate accordingly. A surgical end effector system that moves the instruments to perform a surgical operation and provide force feedback for safety and control of the instrument motion is described herein.

One aspect of the presently disclosed subject matter includes an end effector of a robotic surgery system that includes a fixed plate for attaching an end of a robotic arm, a shaft extending from the fixed plate, a sliding plate moveable relative to the fixed plate along an axial direction of the shaft, a hub assembly mounted to the sliding plate and operatively engaged with the shaft. The hub assembly includes an idler hub, and an inner bearing moveable relative to the idler hub and operatively engaged with the shaft, whereby rotation of the inner bearing moves the sliding plate along the axial direction of the shaft. The end effector further includes a pulley that includes a driven wheel connected to the inner bearing operatively engaged with a motor, whereby rotation of the driven wheel drives rotation of the inner bearing.

In one embodiment, the idler hub circumscribes the inner bearing and is directly mounted to the sliding plate. The hub assembly can include thrust bearings between the idler hub and inner bearing. In one embodiment, the pulley further includes a drive wheel laterally spaced from the driven wheel, an endless belt extending between the drive wheel and driven wheel, and a motor operatively engaged with the drive wheel to drive rotation thereof. In certain embodiments, the pully has a speed ration of at least 2:1. In certain embodiments, the axial direction of the shaft transverses a major plane of the fixed plate.

In certain embodiments, the end effector further includes a base plate attached to the sliding plate, an instrument holder receiver, and a second pulley secured to the base plate and operatively engaged with the instrument holder receiver for imparting a rotary action to the instrument holder receiver. The second pulley can include a second driven wheel operatively engaged with the instrument holder receiver, a second drive wheel laterally offset from the second driven wheel, a second endless belt extending between the second driven wheel and the second drive wheel, and a second motor operatively engaged with the second drive wheel to drive rotation thereof. A rotational axis of the second driven wheel is, in certain embodiments, laterally offset from the axial direction of the shaft.

According to exemplary embodiments, the end effector can further include a pedestal connected to the base plate and the sliding plate, and a transducer secured the base plate and the pedestal. The motor and the second motor can be disposed about a lateral periphery of the pedestal. The motor can be housed within a housing having ports about a lateral side of the housing for receiving inputs.

Another aspect of the presently disclosed subject matter provides an end effector of a robotic surgery system that includes a fixed plate for attaching to a distal end of a robotic arm, a shaft extending from a central location of the fixed plate, and a sliding plate moveable relative to the first plate in an axial direction of the shaft. The end effector can further include a first pulley operatively engaged with the sliding plate, a first motor operatively engaged with the first pulley, a base plate attached to the sliding plate, an instrument holder receiver positioned offset from the shaft, and a second pulley secured to the base plate and operatively engaged with the instrument holder receiver.

According to an exemplary embodiment, the end effector can further include a second motor operatively engaged with the second pulley and laterally offset from the instrument holder receiver. The end effector can further include a pedestal coaxial to the shaft and disposed between the sliding plate and the base plate, and a transducer secured to the pedestal and the base plate. The first motor and the second motor can be disposed about a lateral periphery of the pedestal.

According to an exemplary embodiment, the instrument holder receiver is offset from the shaft in a first direction, and the first motor includes a housing having ports about a lateral side of the housing for receiving inputs, these ports facing a direction generally opposite the first direction.

DETAILED DESCRIPTION

Figure 1:
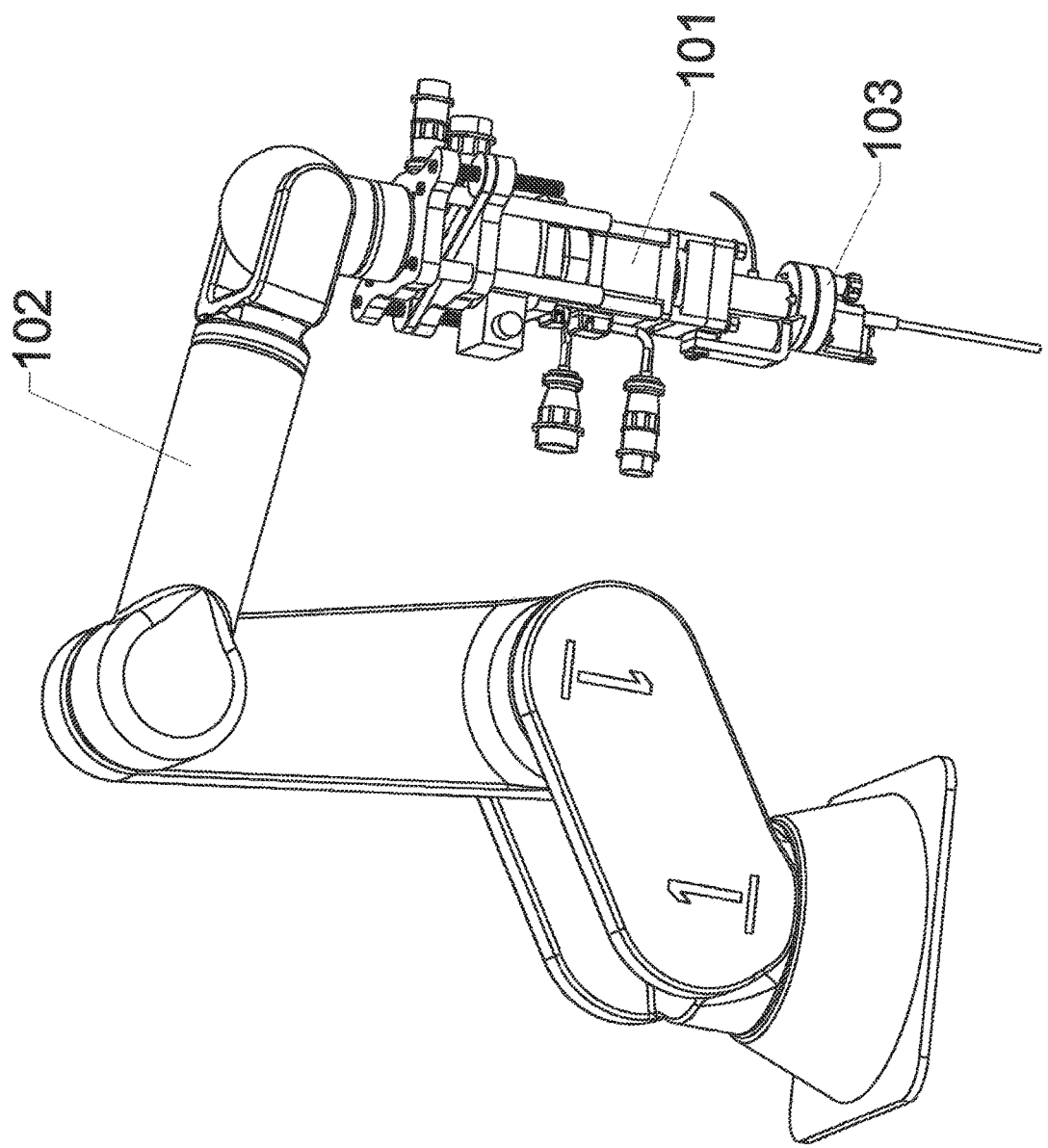
FIG. 1 is an example of a robotic end effector.

This invention is described in the following description with reference to the Figures, in which like reference numbers represent the same or similar elements. While this invention is described in terms of modes for achieving this invention's objectives, it will be appreciated by those skilled in the art that variations may be accomplished in view of these teachings without deviating from the spirit or scope of the present invention. The embodiments and variations of the invention described herein, and/or shown in the drawings, are presented by way of example only and are not limiting as to the scope of the invention.

Unless otherwise specifically stated, individual aspects and components of the invention may be omitted or modified, or may have substituted therefore known equivalents, or as yet unknown substitutes such as may be developed in the future or such as may be found to be acceptable substitutes in the future. The invention may also be modified for a variety of applications while remaining within the spirit and scope of the claimed invention, since the range of potential applications is great, and since it is intended that the present invention be adaptable to many such variations.

In the field of robotics, the end effector or end-of-arm tooling (EOAT) (the terms end effector and EOAT are used interchangeably throughout) may be a device, or devices, attached to the end of a robot arm. The EOAT may allow the robotic system to interact with the environment. The nature of this device may depend on how the EOAT may interact with its environment and the work that needs to be performed by the robotic system. Currently in industrial applications the EOAT may perform a variety of functions.

The EOAT may act like a "hand" of a robotic system; gripping a workpiece that may need to be manipulated or held. This may be accomplished with two or more "fingers" that pinch a workpiece between them, known as impactive gripping. Holding may also be accomplished by means of a vacuum (or an electromagnet), known as astrictive gripping. Ingressive gripping, where pins or some other feature(s) actually penetrate the surface of the object being handled, may be commonly used in the textile industry. Contigutive holding may require direct contact (for example, glue, surface tension, freezing, and the like) and may be used to hold and manipulate low mass objects. The workpiece may also be equipped with a holding feature that engages with the end effector. This may often be done in cases where the workpiece needs to be held accurately and rigidly, such as in the case of a tool or instrument.

The end effector may also be a specific tool or machine for performing a specific job. In many industrial applications, the end effector may be a welding torch that may be used to perform precise and repeatable welds. In other applications, the EOAT may be a paint nozzle for spray painting surfaces or a glue nozzle for applying a bead of glue with precision and repeatability. The end effector may also be a cutting tool used to remove material from a product that is being worked on. The DaVinci medical robotic system has end effectors that consist of forceps, scissors and scalpels. The Robodoc medical robotic system has an end effector that is a milling burr that is used to mill the bone cuts for knee or hip arthroplasty.

The EOAT may also incorporate various sensors. A collision sensor may be incorporated into the end effector (or other part of the robot) to detect collisions and prevent further damage or even injury. Proximity sensors may also be incorporated to detect when the workpiece or another object is near to the end effector. A force sensor may also be incorporated into the end effector to detect forces and moments.

The end effector described herein may be applied to an industrial robotics system that may be used to perform spinal reconstructive surgery. The end effector may have specific capabilities and features that may allow the robotic system to perform surgical steps more effectively and safely. When the robot is performing surgical steps, the end effector may act as the "hands" of a surgeon. The end effector may hold the instrument. The end effector may maneuver the instrument, like a surgeon would, with precision and the appropriate amount of force. The end effector may also detect problems, like the surgeon's hands would, for example, if too much force is encountered during a surgical step. The end effector may also control the force applied to a cutting tool, which is currently done by "feel" by a surgeon, and adjust the feed rate accordingly. A surgical end effector system that moves the instruments to perform a surgical operation and provide force feedback for safety and control of the instrument motion is described herein.

FIG. 1 is an example of a robotic end effector. A robotic end effector 101 may be connected to an industrial robot 102. At the end of the end effector 101 may be an instrument holder 103. The robotic end effector 101 may perform many of the functions a surgeon's hand would perform plus some additional unique functions during surgery.

The end effector 101 may be capable of simultaneously performing rotary action, for example, turning a drill, and axial action, for example, pushing a drill, in a very precise way. These motions may be performed by the end effector 101, requiring no movements by the industrial robot 102. The industrial robot 102 may be used to merely position the end effector 101. The rotational and axial position of the tool may be controlled using servo motors. Linear and rotational position encoders may be incorporated internally to the servo motors or externally to the end effector 101 to provide closed loop feedback of linear and rotational position. The rotational position and axial position may also be controlled relative to each other by the servo motor control and the robotic system control. For example, a pedicle tap with a 2 mm pitch on the threads held within the instrument holder of the end effector 101 may be moved axially by 2 mm for every 360-degrees of rotation.

The torsional force and axial force applied by the servomotors may be measured by a multiaxial force transducer. The measured force may be fed back to the control so that the forces applied by the end effector may be well controlled. For example, in the case of a pedicle tap for a pedicle screw, the axial force applied as the instrument is driven into the pedicle may be measured, as is the torsional force required to turn the tap. These force measurements may be used to determine if there is too much force being applied, for example, in the case of a dull instrument, or if too little force is being applied, for example, in the case of poor bone quality. The end effector may also be able to measure a side-load on the instrument. An instrument may not start cutting into bone immediately, but instead skive off to the side, not making the cut in the intended location. Side-load detection may detect this issue and allow for correction. Skiving may happen in manual robot-guided surgery, resulting in undesirable results. Side load measurement may also be desirable when the robotic system is used to perform a milling or burring operation, for example, burring material from the vertebral endplates in preparation for a lumbar interbody fusion, where the robotic system would apply a side load to the cutting tool during the cutting process. The feed rate of a cutting instrument may be optimized using force measurement feedback.

The end effector may be configured to allow an electric current to be passed through it to the end of the instrument being held to allow for neuromonitoring. An electric current may be applied to the clamped end of the instrument. The clamping mechanism of the instrument holder may be insulated to electrically isolate the instrument being held so that the electric current for neuromonitoring does not shunt to the grounded structure of the instrument holder, end effector or industrial robot itself. The robot control system may be able to perform neuromonitoring on a continuous basis while operating to help prevent nerve damage.

Figure 2:
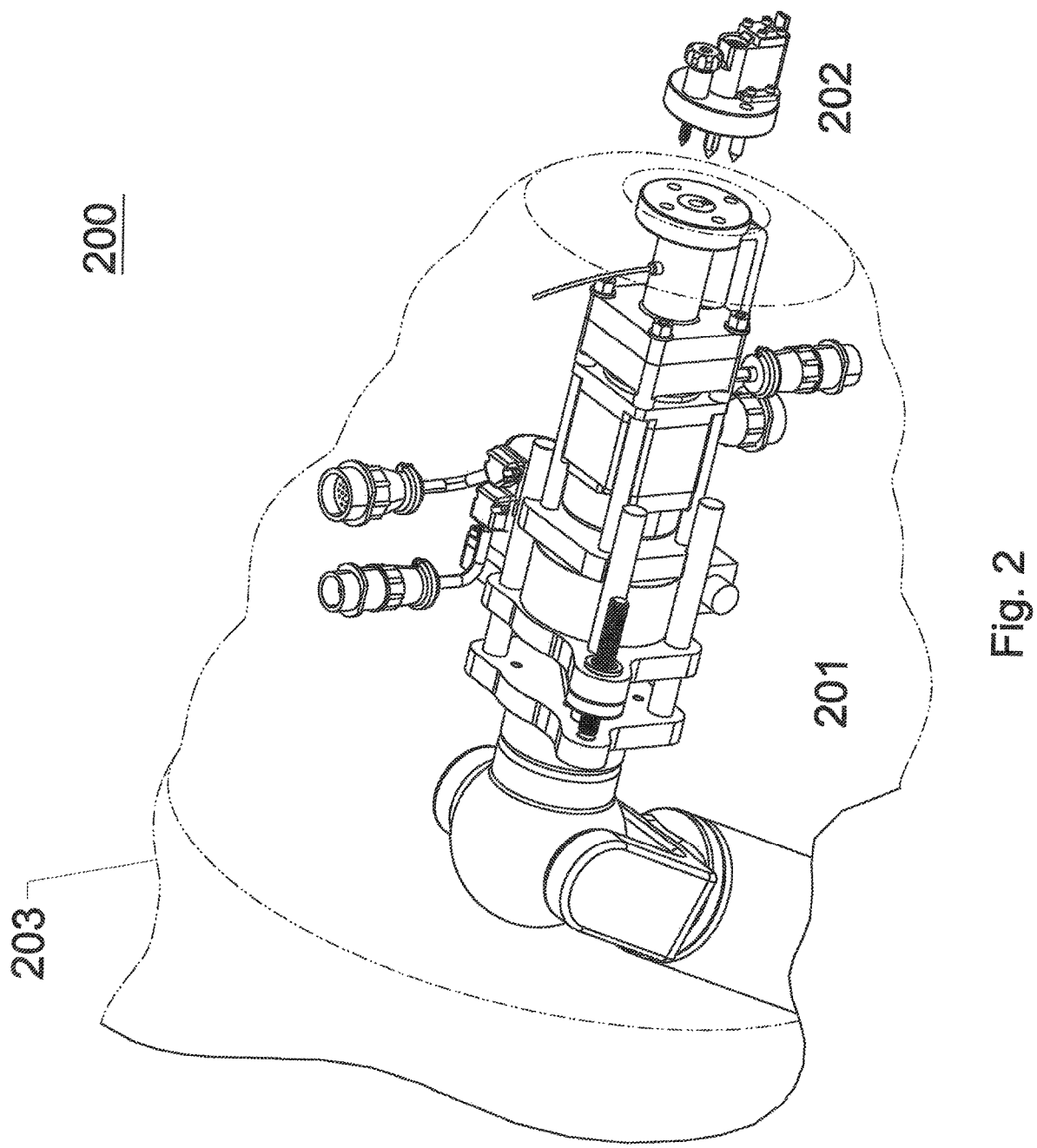
FIG. 2 is an example of the sterile and non-sterile sections of the end effector.

FIG. 2 is an example of the sterile and non-sterile sections of the end effector. The end effector or EOAT 200 may consist of two sections, a non-sterile section 201 and a sterile section 202. The first section 201, the end effector itself, may be non-sterile and covered with a sterile plastic sleeve 203 to prevent contamination of the surgical sterile field. The complexity of the end effector 200 and also the motors and sensors within the device may make sterilization difficult. The industrial robot may also be enclosed in the same sterile plastic sleeve 203. This is the same technique used to cover C-Arm X-ray machines used during surgery. The C-Arm itself is not sterilized but protected with a sleeve. The second section 202, the instrument holder, may be steam sterilized in the same way that surgical instruments are sterilized. The instrument holder may be made from metal and plastic that can withstand sterilization by steam, and may be validated for cleaning and sterilization like any other surgical instrument would be.

The instrument holder may be attached to the end effector with the sterile plastic sleeve in place. The robot may move the end effector into the sterile field where the instrument holder may be attached. The surgical technician may attach the instrument holder to the end effector. The attachment pins for the instrument holder may be pointed to pierce the plastic sleeve when attached to the end effector.

Figure 3:
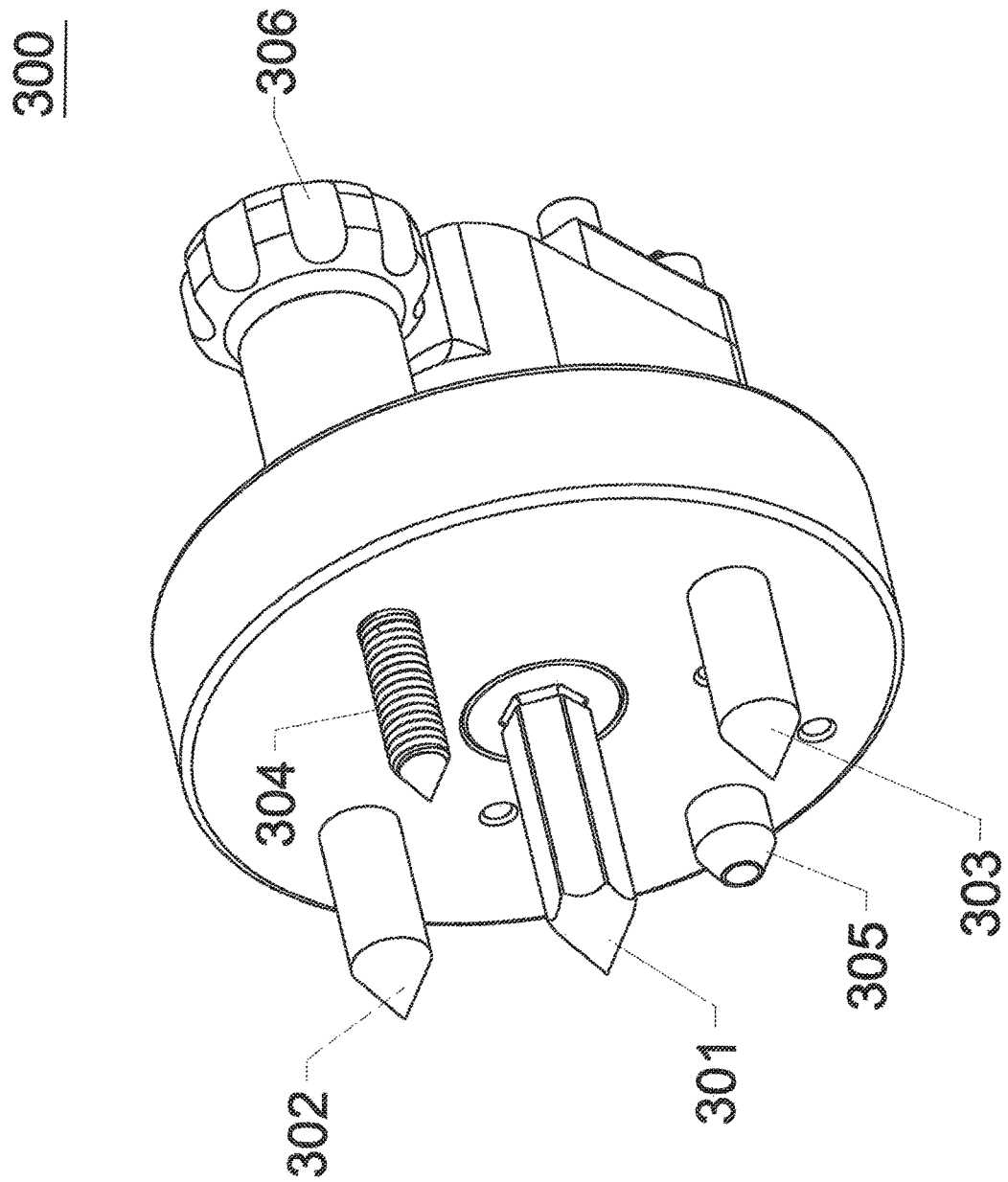
FIG. 3 is an example of a first side of an instrument holder.

FIG. 3 is an example of a first side of an instrument holder. Instrument holder 300 may include five (5) attachment pins. A first pin 301 of the instrument holder may be what passes torque through to the instrument being held. The hexagonal shape mates to a receiving hexagonal shape in the end effector. The first pin 301 may be electrically insulated from the rest of the instrument holder so that a current may be passed through it to the instrument being held and driven for neuromonitoring purposed. Second 302 and Third 303 pins of the instrument holder may be locating pins. These pins 302 and 303 closely fit within receiving holes on the end effector to position the instrument holder in the correct position relative to the end effector. A fourth pin 304 may be a threaded shaft that mates with a threaded receiving hole on the end effector. The fourth pin 304 may be used to securely clamp the instrument holder to the end effector. The knob 306 on the opposite end of the instrument holder may be used to turn the screw. A fifth pin 305 may consist of two parts. The outer sleeve may be hollow and tapered at the end to be able to pierce the sterile plastic sleeve. The inner shaft may be free to move axially within the outer sleeve. The inner shaft may be pushed by a linear solenoid from within the end effector and sterile plastic sleeve to drive a latch that releases or clamps the instrument being held in the instrument holder.

Figure 4:
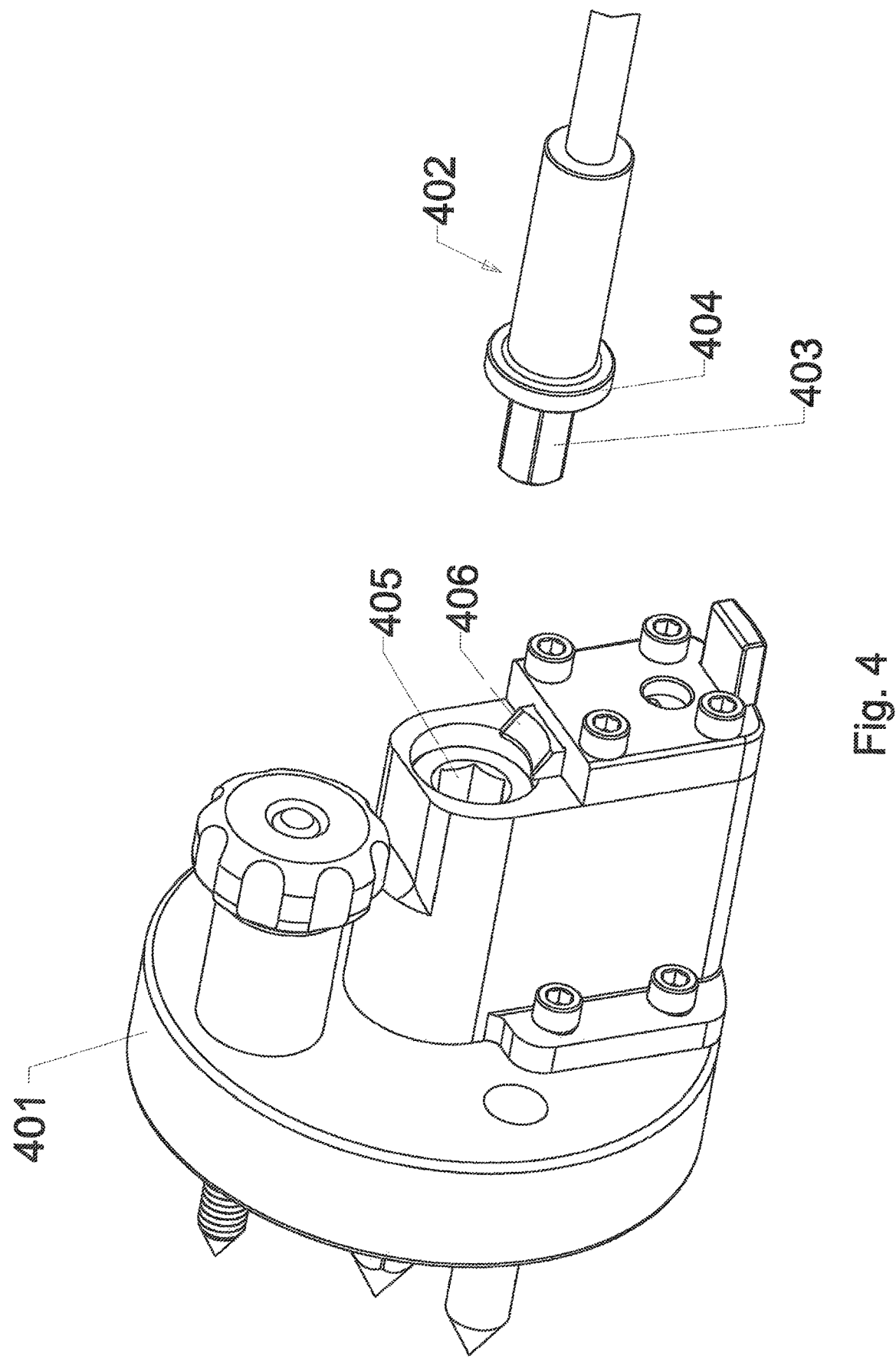
FIG. 4 is an example of a second side of the instrument holder and an instrument for attachment.

FIG. 4 is an example of a second side of the instrument holder and an instrument for attachment. In FIG. 4 an instrument holder 401 and an instrument 402 are shown. Instruments 402 used with the instrument holder 401 may have a hexagonal shape 403 and a collar 404 at the clamped end to mate with the instrument holder 401. The male hexagonal shape 403 on the instrument 402 may be received by the female hexagonal shape 405 on the instrument holder 401. The collar 404 on the instrument 402 may be secured within the instrument holder 401 by a latch 406. The instrument 402 may be inserted into the instrument holder 401 just by pushing it into position, which may be done by a surgical technician or by the robotic system when it "picks up" the instrument from a tool holding rack. The instrument 402 may be released from the instrument holder 401 either by a manual release handle or by the robot, which would energize a solenoid to push the latch 406 to the side. The solenoid may push a tapered wedge that in turn pushes the latch 406 to the side, releasing the instrument 402 from the instrument holder 401.

Figure 5:
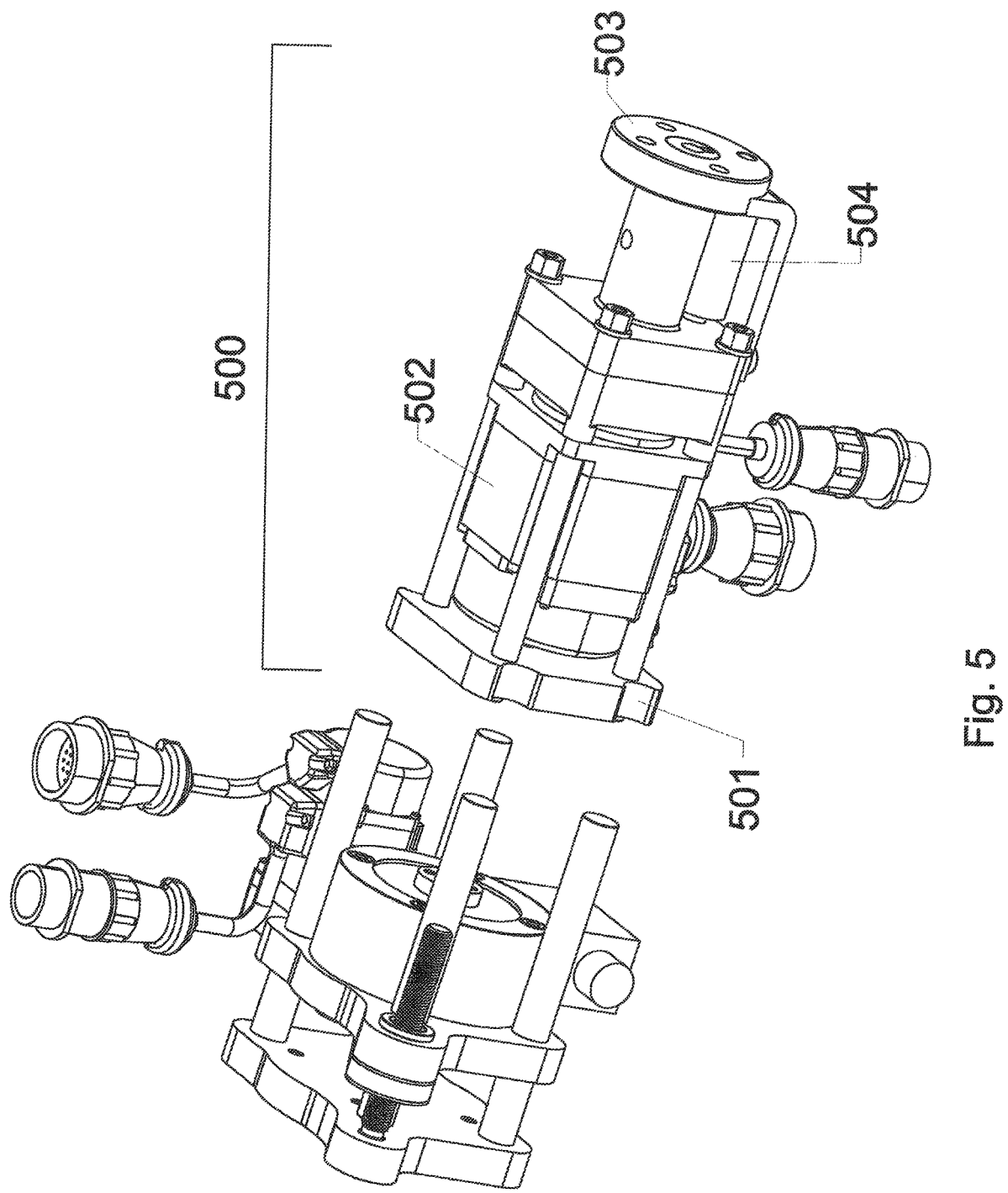
FIG. 5 is an example of a front section of the end effector.

FIG. 5 is an example of a front section of the end effector. The front section 500 of the end-effector may consist of a rigid frame 501 that holds a servomotor 502 (that provides a torsional driving force), a conical bearing (shown in FIG. 6) that protects the servomotor 502 from thrust and side-load, a receiver (shown in further detail in FIG. 6) 503 for the instrument holder, and a solenoid 504 for latching and unlatching an instrument from the instrument holder.

Figure 6:
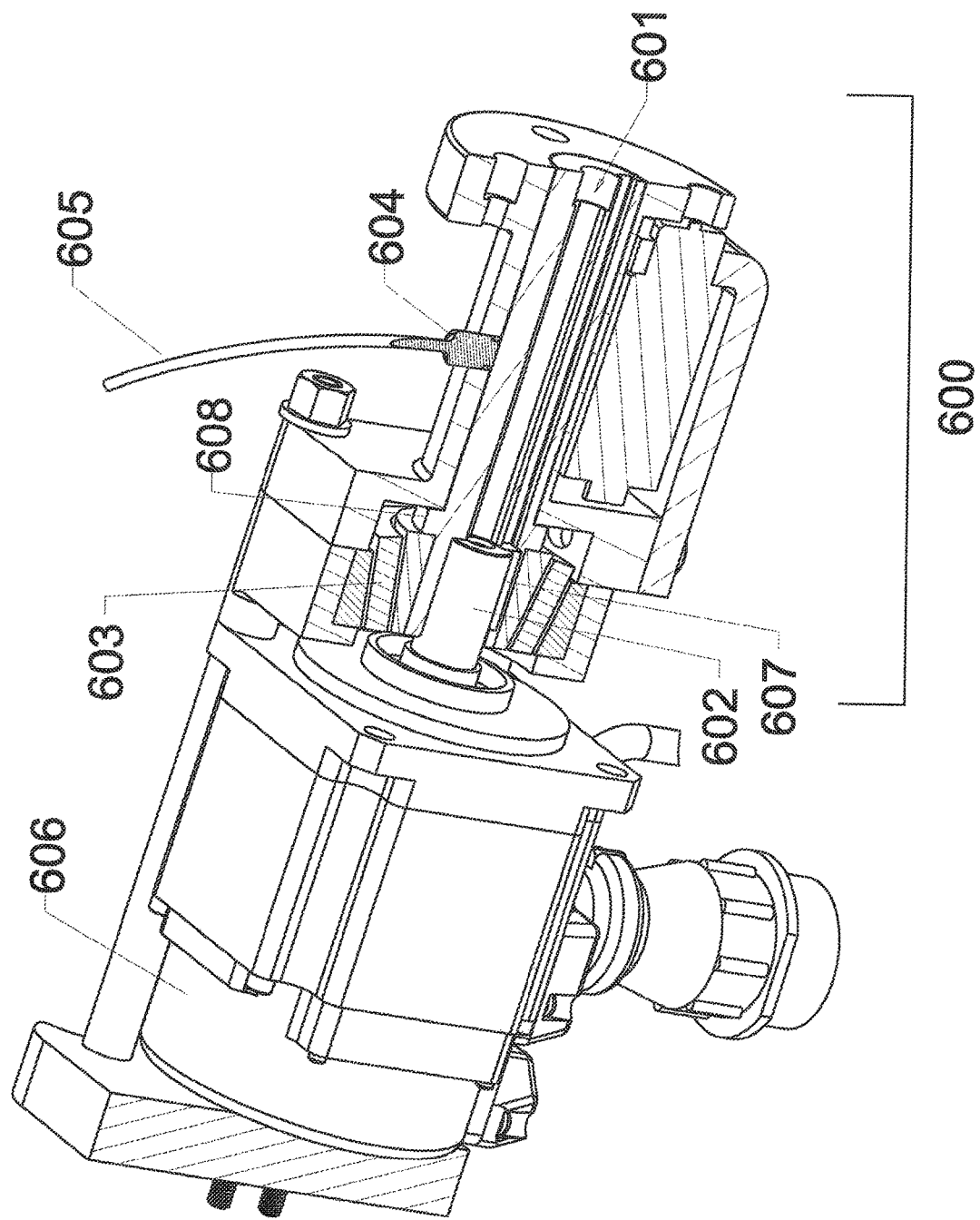
FIG. 6 is an example of inside the receiver for the instrument holder.

FIG. 6 is an example of inside the receiver for the instrument holder. Housed within the receiver 600 for the instrument holder is a driveshaft 601 that transmits torque from the servomotor 606 to the instrument holder. The driveshaft 601 may be connected to the servomotor shaft 602 so that rotational forces may be transmitted from the servomotor 606 to the driveshaft 601; however thrust forces are not transmitted. A key 607 between the servomotor shaft 602 and the driveshaft 601 transmits rotational force only. A collar 608 on the driveshaft 601 may transmit thrust to the conical bearing 603. The thrust and side-load may be transmitted through the conical bearing 603 directly to the front rigid frame of the end effector. The driveshaft 601 may be electrically insulated from the rest of the front rigid frame so that an electric current may pass from the instrument being driven, through the driveshaft 601, to a brush 604 connected to a wire 605 for neuromonitoring.

Figure 7:
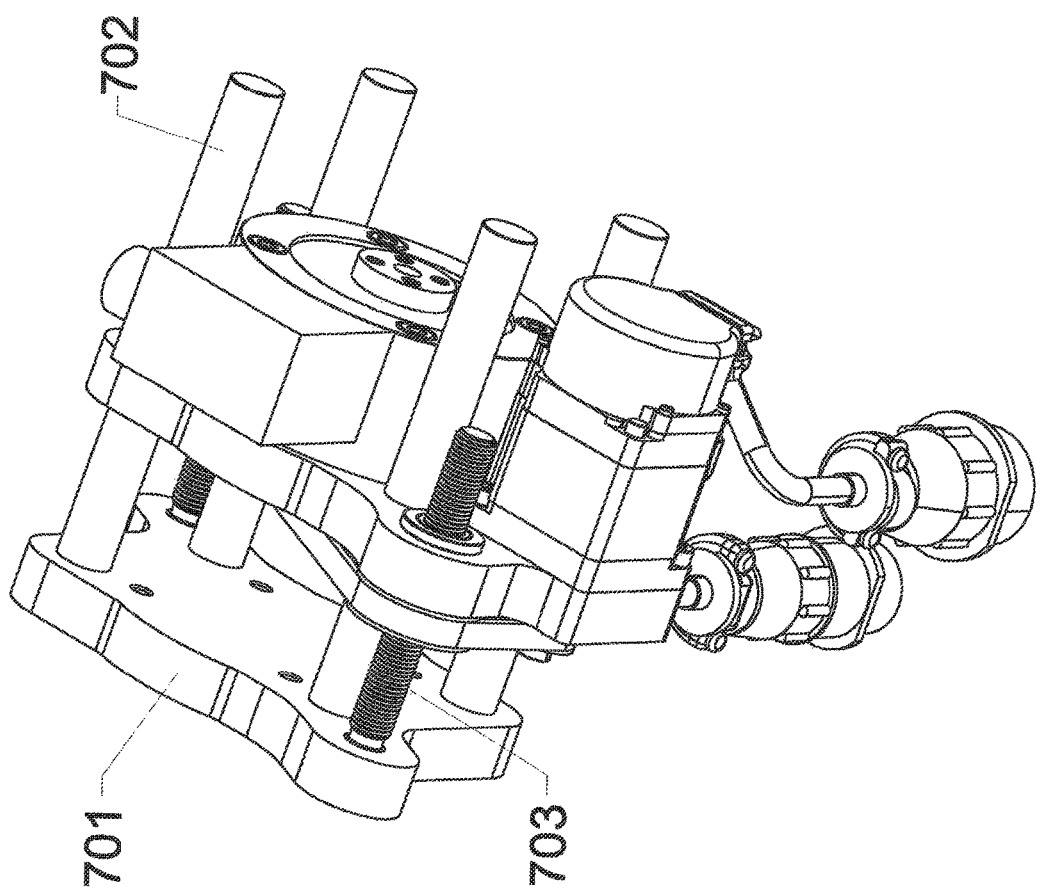
FIG. 7 is an example of a first view of a back section of the end effector.

FIG. 7 is an example of a first view of a back section of the end effector. The back section 700 of the end effector may be rigidly attached to the final segment of the industrial robot arm at a fixed plate 701. This connection may be tailored to fit the connection features of the industrial robot used in the robotic system. One or more smooth shafts 702 and one or more externally threaded shafts 703 may be rigidly attached to the fixed plate 701. These shafts 702 and 703 may be used to guide and move a sliding plate (shown in FIG. 8) and the components attached to it.

Figure 8:
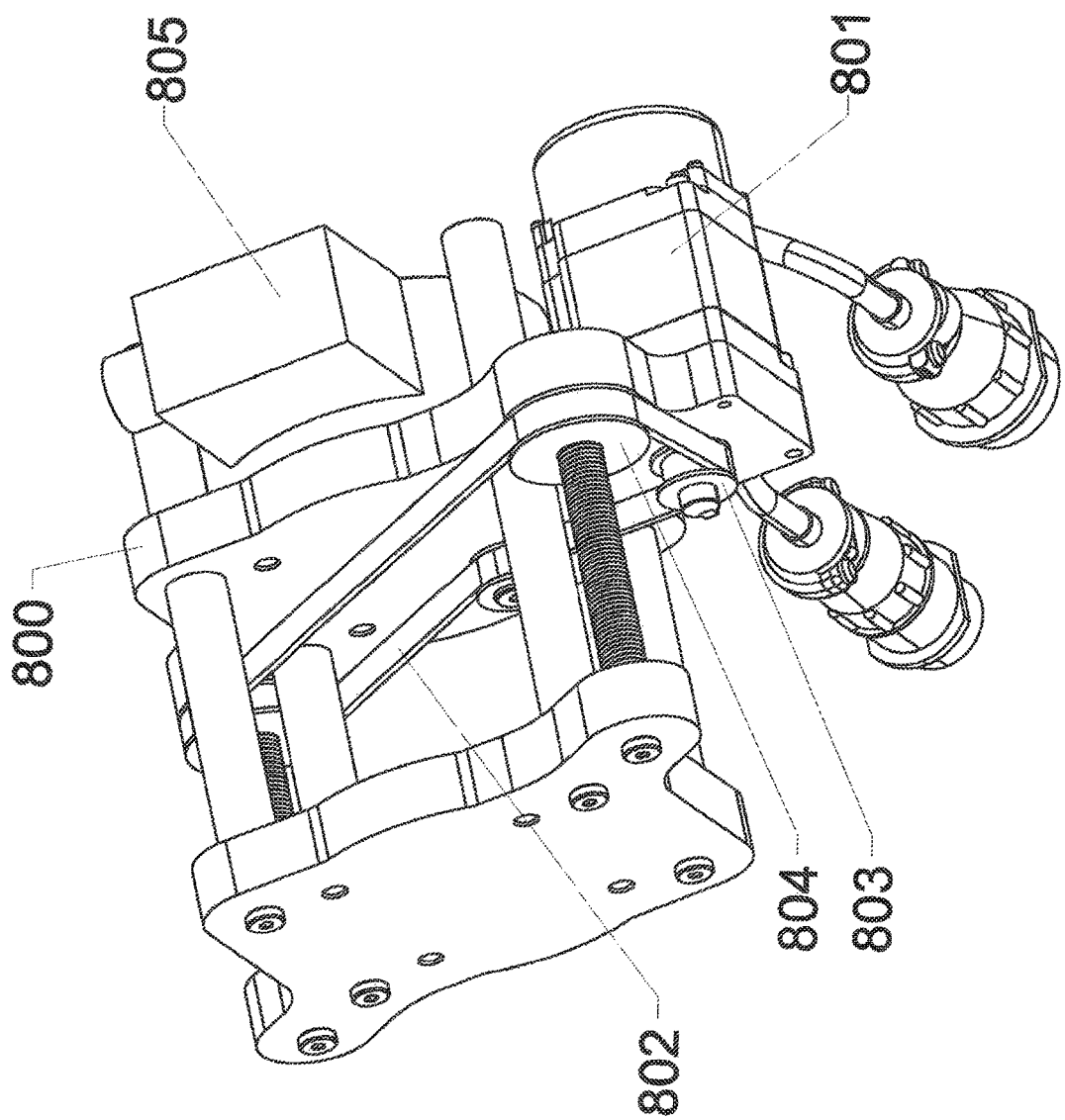
FIG. 8 is an example of a second view of the back section of the end effector.

FIG. 8 is an example of a second view of the back section of the end effector. The sliding plate 800 may move axially along the shafts attached to the fixed plate. A servomotor 801 may be used to drive and control this axial motion. The rotation of the servomotor 801 may be transmitted to one or more internally threaded pulleys or cogs 804 through a timing belt or endless belt 802. A pulley or cog 803 may be rigidly attached to the shaft of the servomotor 801 to drive the timing belt or endless belt 802. The timing belt or endless belt 802 may drive one or more internally threaded pulleys or cogs 804. These internally threaded pulleys or cogs 804 may have teeth to receive the timing belt or endless belt 802 and may be fixed to the sliding plate 800 so that they can rotate about their axis but not move in any other degree of freedom relative to the sliding plate 800. The internally threaded wheels may be threaded onto the externally threaded shafts so that turning them may cause the sliding plate 800 to move relative to the fixed plate as guided by the smooth shafts. The drivetrain may allow the rotational motion of the servomotor 801 to cause axial motion of the sliding plate 800. The servomotor 801 and a controller may control the position, velocity, and acceleration of the sliding plate 800. The servomotor 801 body may be rigidly mounted to the sliding plate 800 so that the shaft of the servomotor 801 may pass through a clearance hole in the sliding plate 800. A multiaxial transducer 805 may also be rigidly mounted to the sliding plate 800.

Figure 9:
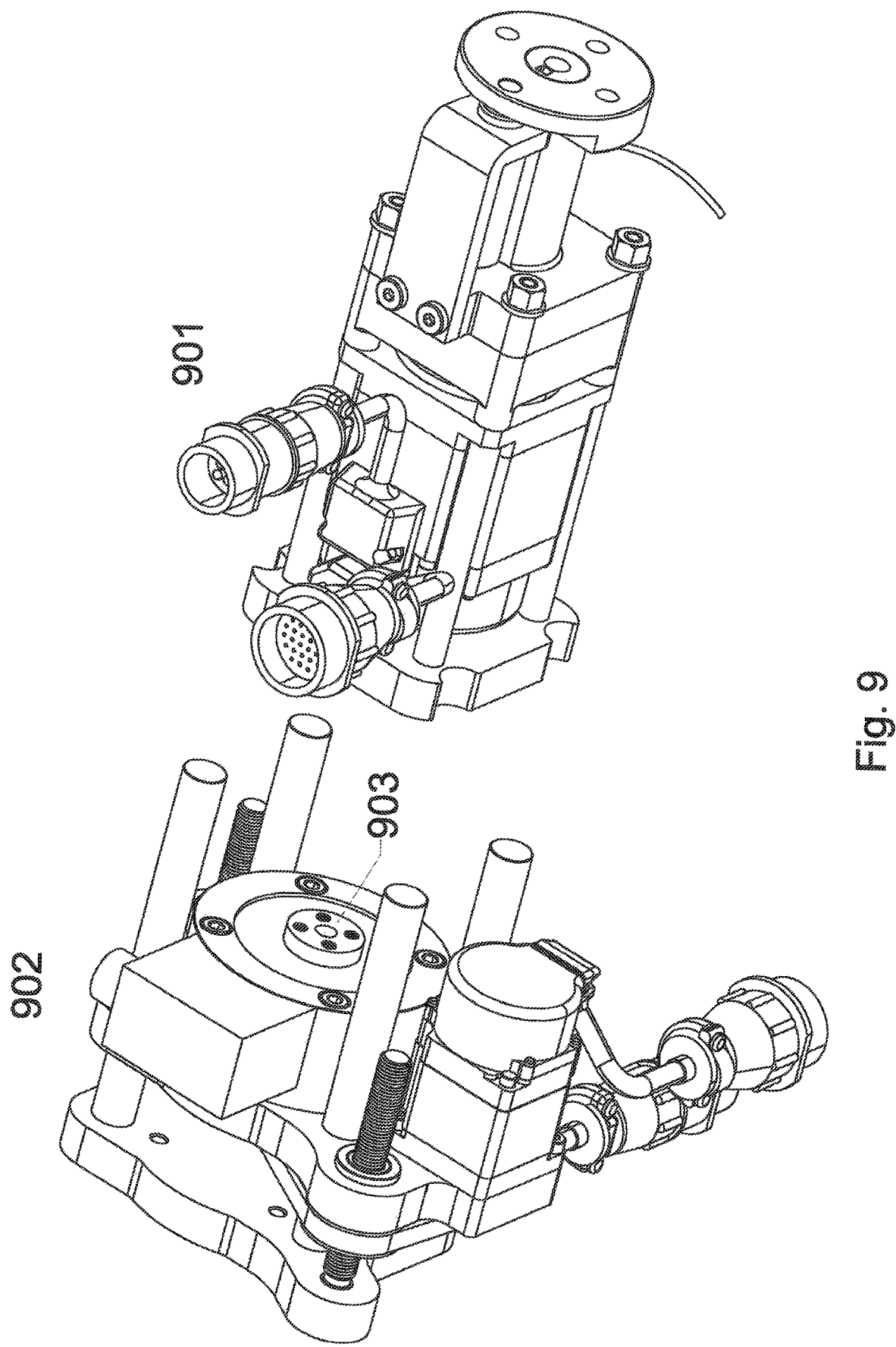
FIG. 9 illustrates the front section and the back section of the end effector being connected.

FIG. 9 illustrates the front section and the back section of the end effector being connected. The front section 901 of the end effector may rigidly attached to the back section 902 of the end effector at a load mounting point 903 of the multiaxial transducer. All degrees of freedom between the front section 901 of the end effector and the back section 902 of the end effector may be constrained by the multiaxial force transducer. With this configuration, all torsional forces, axial forces and side-load forces may be transmitted directly to the multiaxial force transducer.

FIGS. 10-19 illustrate another exemplary embodiment of an end effector in accordance with the subject disclosure. The end effector, shown in tandem in FIG. 10 as two end effectors 1000A and 1000B, can be rigidly attached or otherwise secured or engaged with an end of a robotic arm 205 via a fixed plate 1101. A plastic sleeve 203 may be provided as explained above to separate non-sterile and sterile sections of the end effector.

Figure 10:
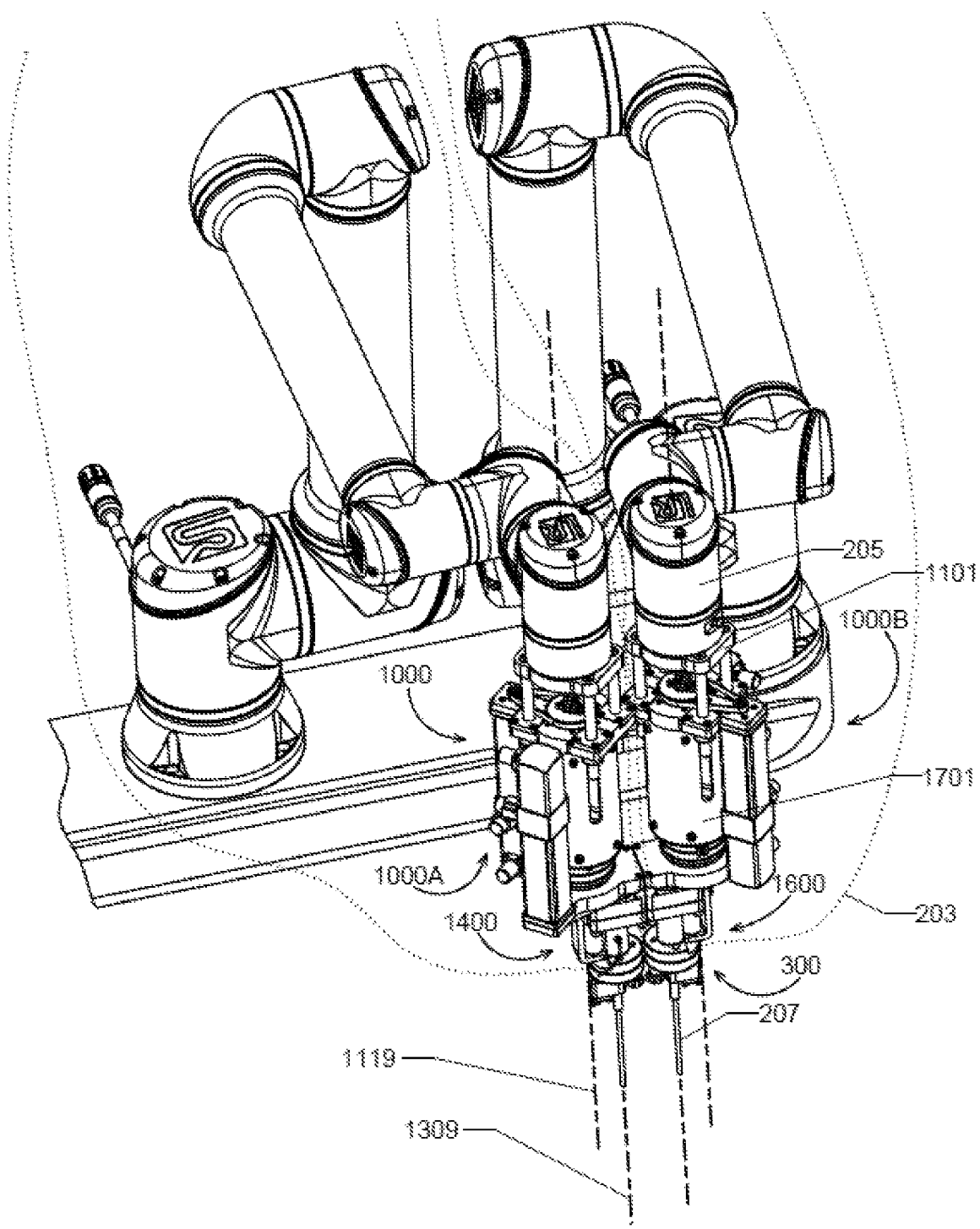
FIG. 10 is a perspective view of two end effectors operating in tandem according to an exemplary embodiment.

As shown in FIG. 10, the end effector includes a back or first section 1100 for moving the end effector in an axial direction, a front or second section 1400 for applying a rotary action or torque to an instrument 207 via an instrument holder 300 located in the sterile section, and instrument holder receiver 1600 located in the non-sterile section. A pedestal 1701 is disposed between the back or first section 1100 and the front or second section 1400.

Figure 11:
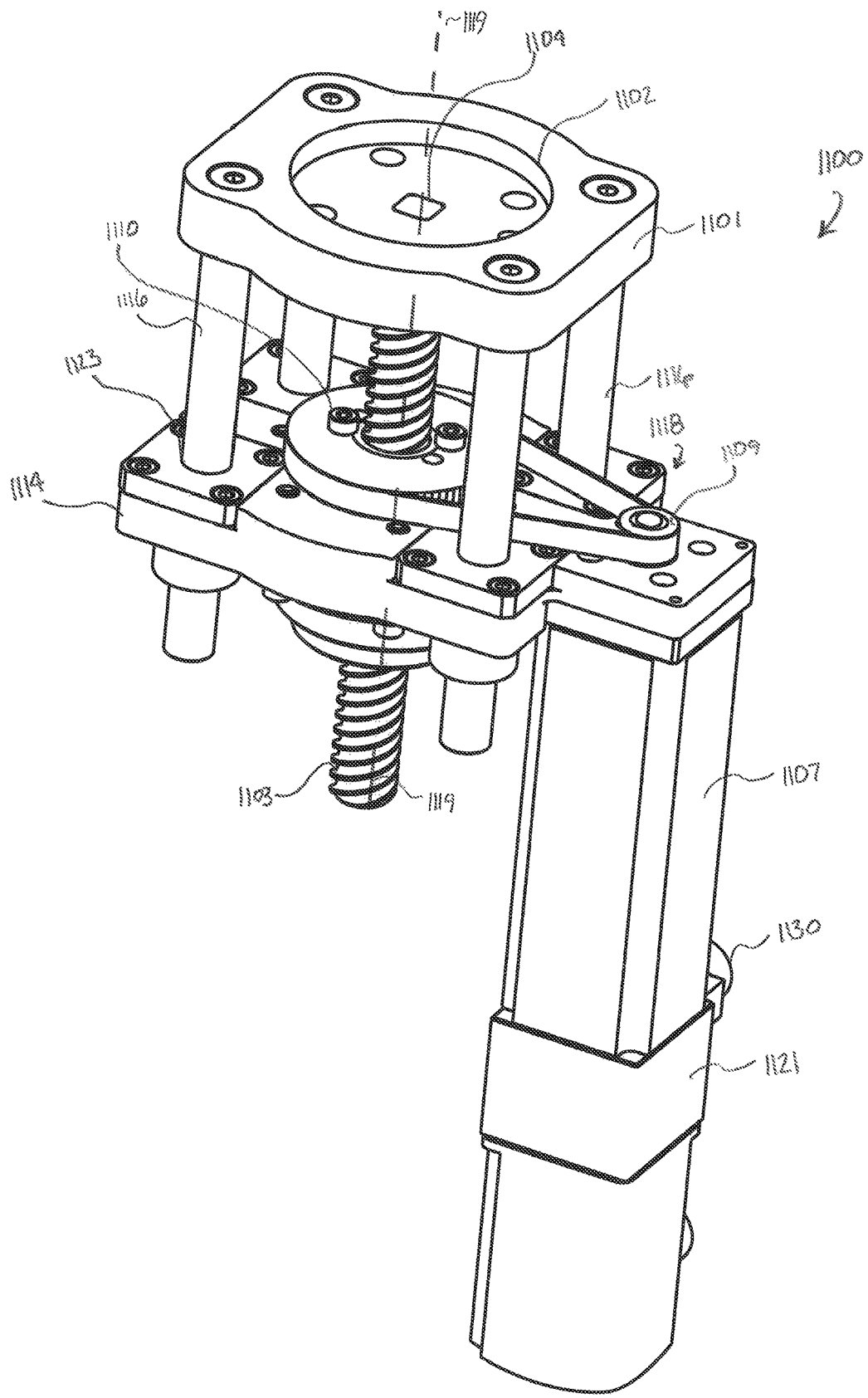
FIG. 11 is a perspective view of a back or first section of an end effector in accordance with an exemplary embodiment of the present disclosure.
Figure 12:
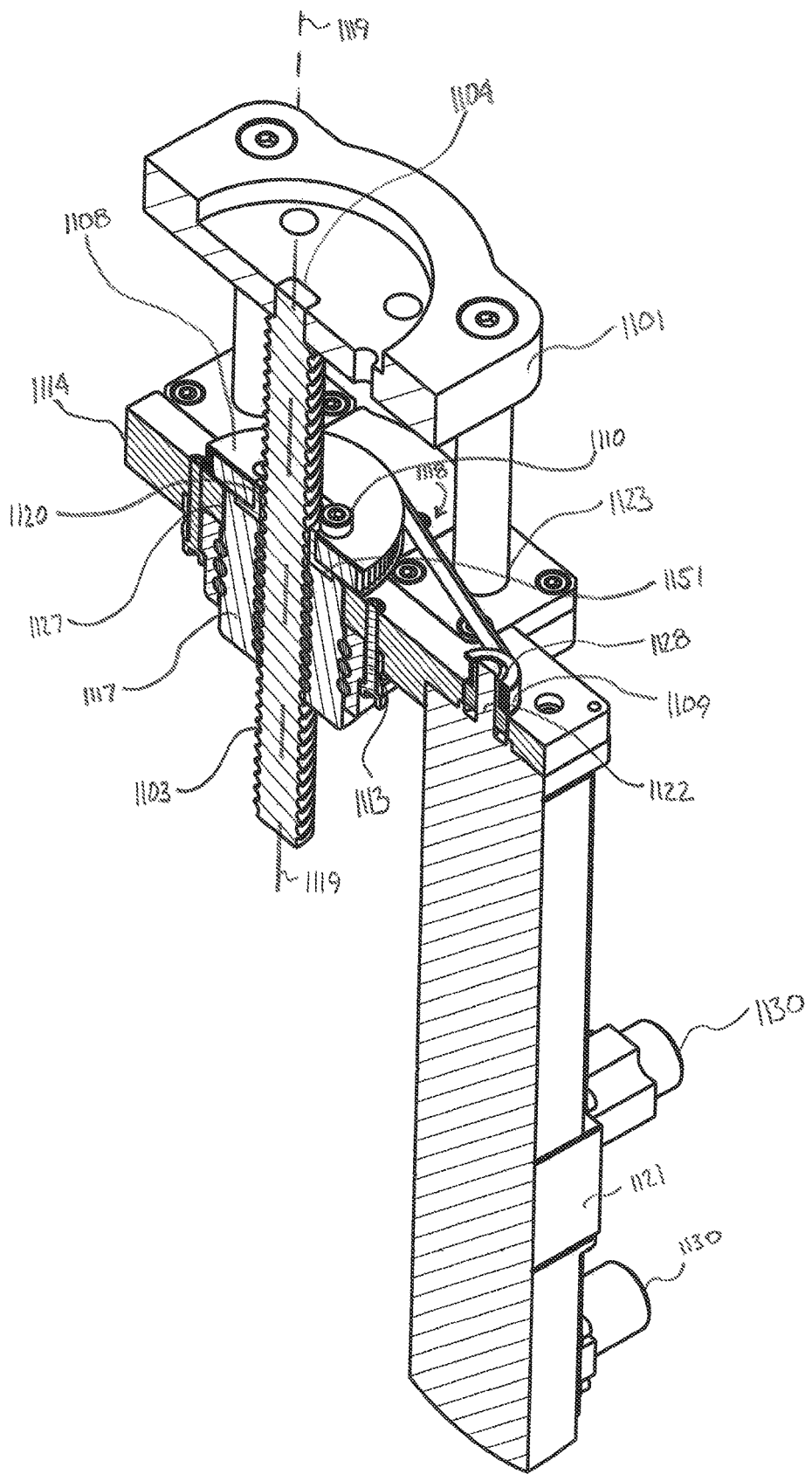
FIG. 12 is a cross-sectional view of the back or first section of FIG. 11.
Figure 13:
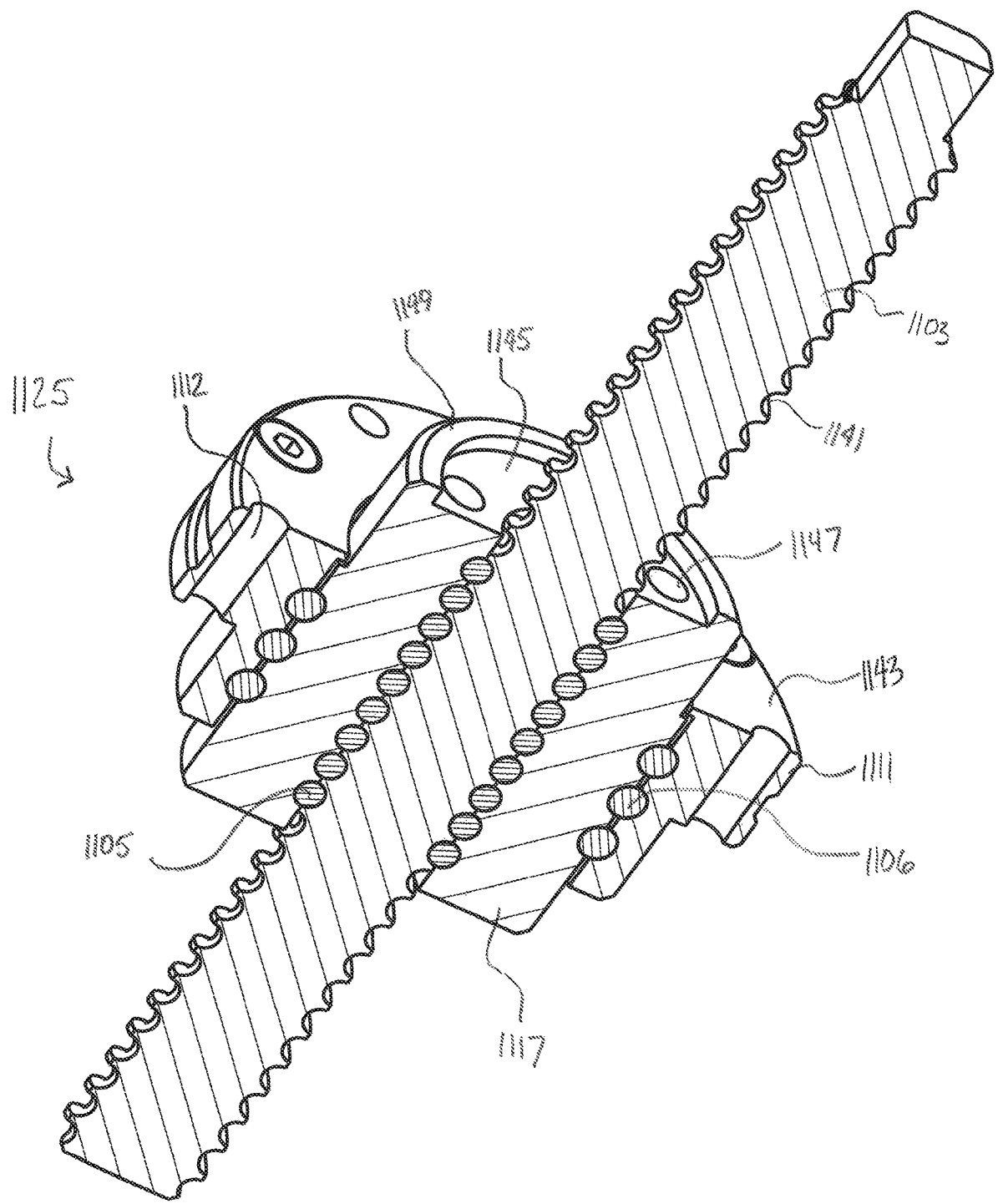
FIG. 13 is a cross-section of a hub assembly of FIG. 11.

FIGS. 11-13 depict the back or first section 1100 for moving the end effector in an axial direction. The fixed plate 1101 is configured as best shown in FIG. 11 and includes a substantially planar body. The fixed plate includes a recess 1102, which can assist to secure the fixed plate 1101 to the end of the robotic arm 205. The fixed plate also includes window 1104 about its center within which a shaft 1103 is received. As further discussed below, the fixed plate 1101 is connected to a sliding plate 1114.

The shaft 1103 is configured as best shown in FIGS. 11-13. In the present exemplary embodiment, the shaft is a threaded or grooved shaft that extends from the fixed plate 1101 having a longitudinal axis that transverses a major plane of the fixed plate 1101. The shaft 1103 extends from a central location of the fixed plate 1101 and defines a central axis 1119. The proximal end of the shaft includes a head having a substantially square shaped cross-section, complementarily shaped to that of the widow 1104. The shaft has an overall length sufficient to connect to the sliding plate 1114 and to encompass the desired axial movement of the end effector 1000.

The shaft 1103 can be an externally threaded or grooved shaft that extends from a central location of the fixed plate 1101 about a central axis 1119. Central axis 1119 is coaxial with an axial direction of the shaft 1103. Grooves or, more particularly in certain exemplary embodiments, helical raceways 1141 are provided externally about the shaft that are shaped to complement ball bearings 1105 as further discussed below.

The sliding plate 1114 is configured as best shown in FIGS. 11 and 12. One or more smooth shafts 1116 are provided that connects the sliding plate to the fixed plate 1101. In the present exemplary embodiment, four equally spaced smooth shafts 1116 extend from the outer regions of the fixed plate 1101. The smooth shafts 1116 are rigidly attached to the fixed plate 1101 and serve to guide and properly position the sliding plate 1114 as the sliding plate moves upward or downward along the smooth shafts 1116 in an axial fashion relative to the fixed plate 1101. The sliding plate 1114 includes clearance holes 1123 to receive the smooth shafts 1116, a central clearance hole 1127 to accommodate the shaft 1103 and a hub assembly 1125, and a drive wheel clearance hole 1128.

A pulley 1118 is disposed on the sliding plate as shown in FIGS. 11 and 12. The pulley 1118 includes a drive wheel 1109, a driven wheel 1108 and an endless belt 1115 extending between the drive wheel 1109 and the driven wheel 1108. The driven wheel 1108 and drive wheel 1109 can each be provided with projections, indentations or other shapes along its outer perimeter designed to engage complimentary indentations, projections or shapes provided on the interior surface of a endless belt 1115 to maintain a constant engagement between the endless belt 1115 and the driven wheel 1108 and drive wheel 1109. The driven wheel 1108 is centrally located about the shaft 1103 and central axis 1119. The drive wheel 1109 is positioned within the drive wheel clearance hole 1128. For example, the driven wheel 1108 and drive wheel 1109 can be sized such that the ratio of the driven wheel diameter to the drive wheel diameter is greater than, or equal to, or greater than or equal to, 5:1, 4:1, 3:1, 2:1, or 1.5:1.

The hub assembly 1125 is also centrally located about the shaft 1103 and central axis 1119. The hub assembly operatively moves the sliding plate 1114 along the axial direction of the shaft and includes an idler hub 1111 and an inner bearing 1117 that is mounted within the idler hub 1111. As best shown in FIG. 13, thrust bearings 1106 are positioned between the idler hub 1111 and inner bearing 1117, and ball bearings 1105 are positioned between the shaft 1103 and inner bearing 1117. The thrust bearings 1106 serve to manage the friction between the idler hub 1111 and the inner bearing 1117 as the inner bearing 1117 rotates about the shaft 1103. As explained in greater detail below, the idler hub 1117 is fixedly mounted to the sliding plate 1114.

As best shown in FIGS. 11-13, the driven wheel 1108 engages the inner bearing 1117 at a recessed, top flat face 1145, recessed from a raised portion 1149 along the perimeter of the face 1145. Flat face 1145 is provided with bores 1147 to receive socket-head screws 1010 to operatively engage the driven wheel 1108 to the inner bearing 1117. Mount 1120 is provided to circumscribe the shaft 1103 and is provided with a flange 1151 shaped to complement face 1145 and raised portion 1149. Mount 1120 contains a through hole (not shown) to complement bores 1147. Socket-head screw 1110 is received by bore 1147 to join driven wheel 1108 to inner bearing 1117 to allow rotation imparted by driven wheel 1108 to be imparted to the inner bearing 1117. In this particular embodiment, the driven wheel 1108 serves to drive rotation of the hub assembly 1125.

As shown in FIG. 13, the idler hub 1111 is provided with a planar face 1143 along its top surface. Sliding plate 1114 is secured to the idler hub 1111 along this planar face 1143 which is provided with through holes 1112 to receive socket-head screws 1113. Socket-head screw 1113 secures the idler hub 1011 to the sliding plate 1114, and allows the sliding plate 1114 to move along the axial direction of the shaft 1103 as the inner bearing 1117 rotates about the shaft 1103. Other methods of engaging the hub assembly 1125 to sliding plate 1114 will present themselves to one of ordinary skill in the art, and can be employed in accordance with the presently disclosed subject matter.

The inner bearing 1117 is internally provided with ball bearings 1105 that engage with the grooves or helical raceways 1141 of the shaft 1103. The grooves 1141 are dimensioned to receive the ball bearings 1105. Depending on the orientation of the grooves, rotation of the inner bearing 1117 about the shaft 1103 shaft in a direction (e.g., clockwise) causes the hub assembly 1125 to travel in one direction along an axial direction of the shaft (e.g., up as oriented in FIG. 12) and rotation of the inner bearing 1117 in an opposite direction (e.g., counter-clockwise) causes the hub assembly 125 to travel in the opposite direction along the axial direction of the shaft (e.g., down as oriented in FIG. 12).

In this particular exemplary embodiment, a motor 1107 is provided about a lateral periphery of back or first section 1100 and provides a rotational force to the drive wheel. The motor 1107 is provided with a housing 1121 that includes one or more ports 1130 for wiring and other inputs. In this particular embodiment, the motor 1107 is a servomotor connected to a distally facing side of the sliding plate. The drive wheel 1109 is provided in proximity to the motor 1107 and is rigidly attached to a shaft 1122 of the motor 1107, whereby rotation of the shaft 1122 is transferred to rotate the drive wheel 1109. Other configurations could be employed such that rotational motion provided by a motor is transmitted to pulley 1118, including alternative configurations to rotate drive wheel 1109 and/or driven wheel 1108 in a clockwise and counter-clockwise fashion.

In operation, the motor 1107, in communication with a controller (not shown), provides a clockwise or counter-clockwise rotational force to rotate drive wheel 1109 clockwise or counter-clockwise. Rotation of the drive wheel 1109 drives the endless belt 1115 to rotate the driven wheel 1108, which in turn causes rotation of the inner bearing 1117 by virtue of the engagement of the driven wheel 1108 to the inner bearing 1117 at the face 1145 of the inner bearing 1117, via mount 1120. Rotation of the inner bearing moves the inner bearing 1117, and thus the sliding plate 1114 about the shaft 1103 upward or downward in the axial direction of the shaft 1103 depending on the direction (clockwise or counterclockwise) of the rotation of the inner bearing 1117 about the shaft 1103. Due to the design of this particular exemplary embodiment, and particularly hub assembly 1125, backlash will be reduced.

Figure 14:
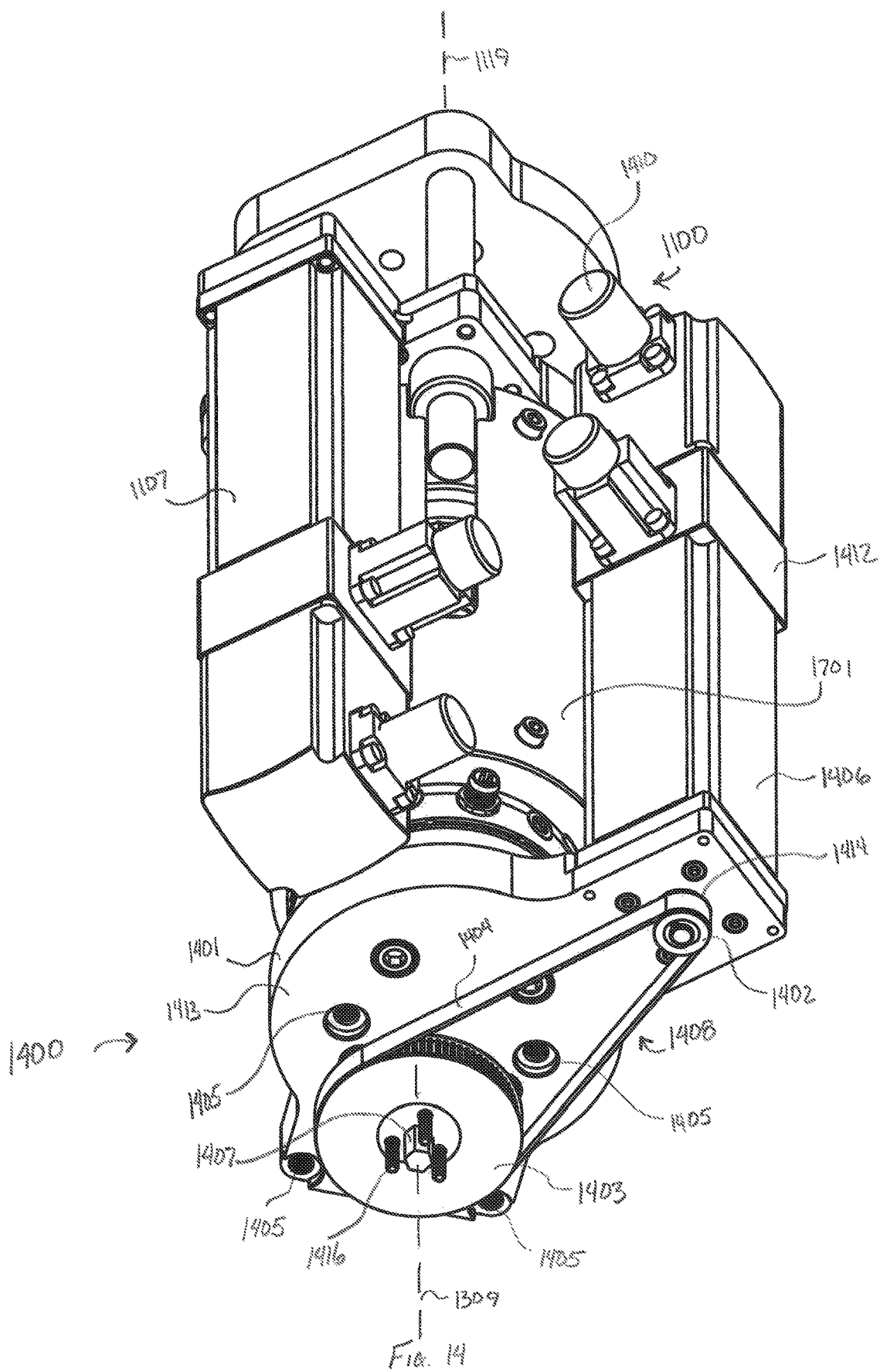
FIG. 14 is a perspective view of the back or first section of FIG. 11 and a front or second section according to an exemplary embodiment.

FIG. 14 depicts a front or second section 1400 according to an exemplary embodiment, shown attached to the back section 1100 via a pedestal 1701. The front or second section 1400 includes a base plate 1401, a second pulley 1408 along a first or distally facing planar surface 1413 of the baseplate 1401, and a second motor 1406 along the periphery of the pedestal 1701. A housing 1412 of the second motor 1406 is provided that includes one or more ports 1410 about its lateral sides for wiring and other inputs.

Figure 17:
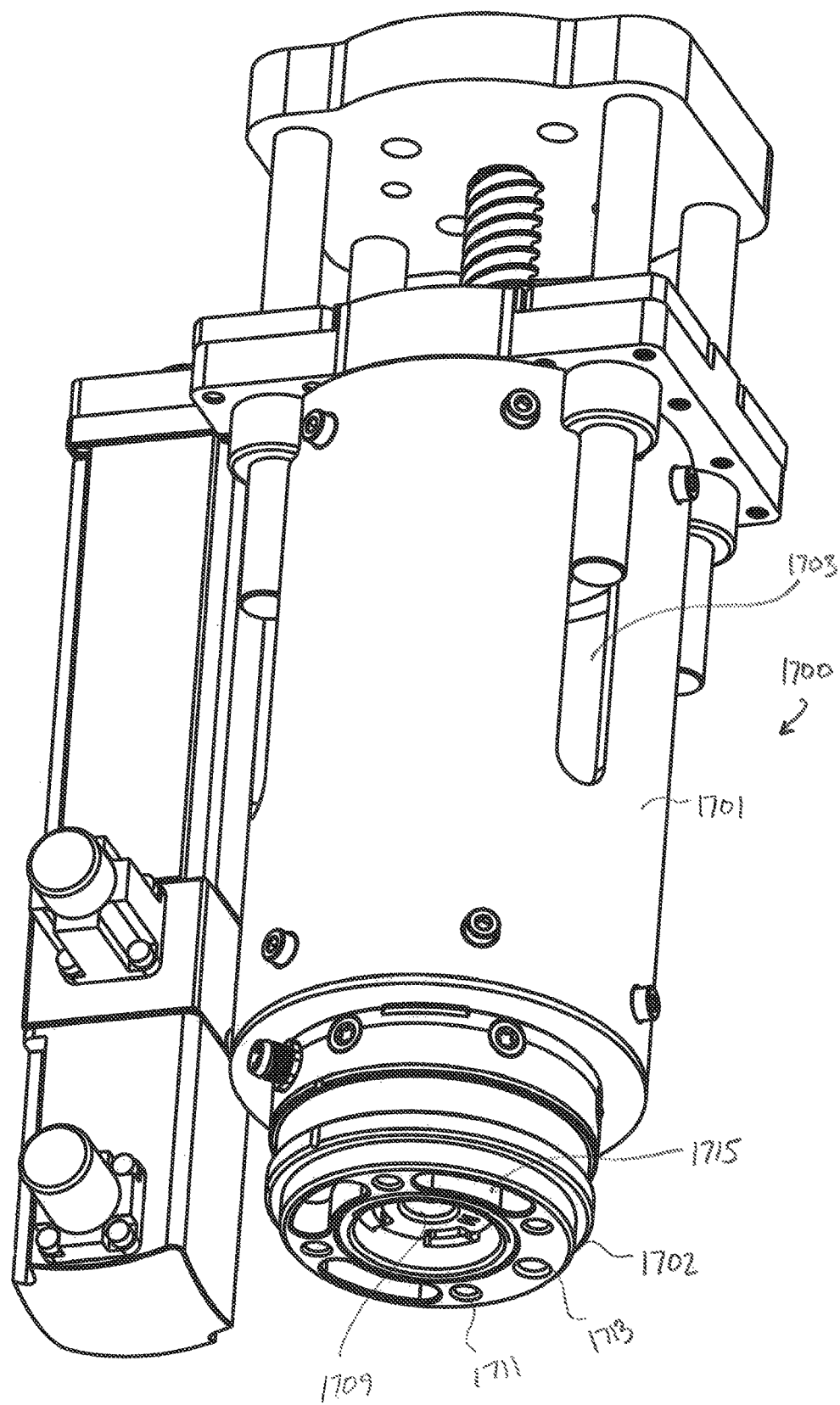
FIG. 17 depicts a perspective view of the back or first section of FIG. 11 attached to a pedestal system.

The base plate 1401 includes apertures 1405 for securing support shafts 1604 to the instrument holder receiver 1600 along the first surface 1413 of the base plate 1401. The base plate 1401 is secured to a transducer 1702 along a proximally facing or second surface 1411 of the base plate 1401 (FIG. 17). The transducer 1302 is engaged with the top or second surface 1411 of the base plate 1401 about the central axis 1119, which is defined by the center of the shaft 1103. Base plate 1401 further includes a clearance aperture 1414 to accommodate a drive wheel to a second pulley 1408, which is operatively engaged with the second motor 1406.

Located on the distally facing or first surface 1413 of the base plate 1401 is the second pulley 1408. Second pulley 1408 includes a second drive wheel 1402, a second driven wheel 1403, and a second endless belt 1404 extending between the second drive wheel 1402 and the second driven wheel 1403. The second drive wheel 1402 and second driven wheel 1403 can be provided with projections, indentations or other shapes designed to engage complimentary indentations, projections or shapes provided on the interior surface of second endless belt 1404 to maintain a constant engagement between the second endless belt 1404 and the second drive wheel 1402 and second driven wheel 1403.

The sizes of the second drive wheel 1402 and second driven wheel 1403 can be adjusted to provide the proper mix of torque and rotational speed. More particularly, according to a feature of this particular embodiment, the sizes of second drive wheel 1402 and second driven wheel 1403 can be adjusted to "gear down" and generate more torque with less revolutions per minute (or less torque with more revolutions per minute). For example, if more torque and less revolutions per minute are desired, one could increase the size of second driven wheel 1403 or if less torque and more revolutions per minute are desired, one could increase the size of second drive wheel 1402. For example, the second driven wheel 1403 and second drive wheel 1402 can be sized such that the ratio of the second driven wheel diameter to the second drive wheel diameter is greater than, or equal to, or greater than or equal to 5:1, 4:1, 3:1, 2:1, or 1.5:1.

Referring to FIG. 14, a hexagonal shaped male prong 1407 is centrally provided about second driven wheel 1403 and about axis 1309. A plurality of locator pins 1416 are disposed equidistant from the male prong 1407. Rotation of second driven wheel 1403 rotates the male prong 1407 and locator pins 1416, thereby imparting a rotary action and torque to attachments that are attached to the male prong 1407, such as the instrument receiver 1600, and consequently the instrument holder 300 and the instrument 207 itself. The drive shaft 1601, which is also disposed about axis 1309, is internally provided with a shape complementary to the hexagonal shape of the male prong 1407 for connection therewith.

Figure 15:
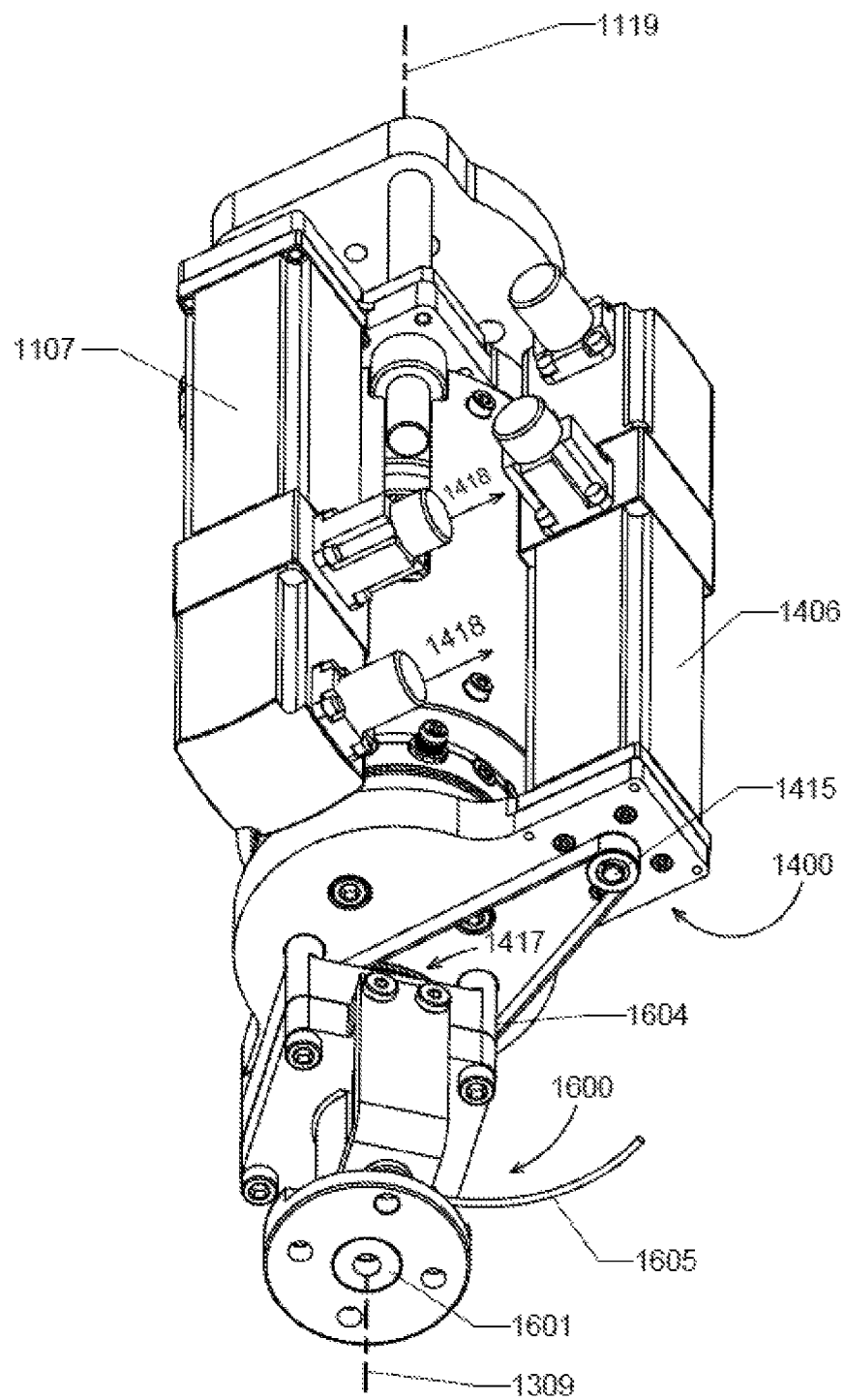
FIG. 15 is a perspective view of the end effector shown in FIG. 14, attached to an instrument holder receiver.
Figure 16:
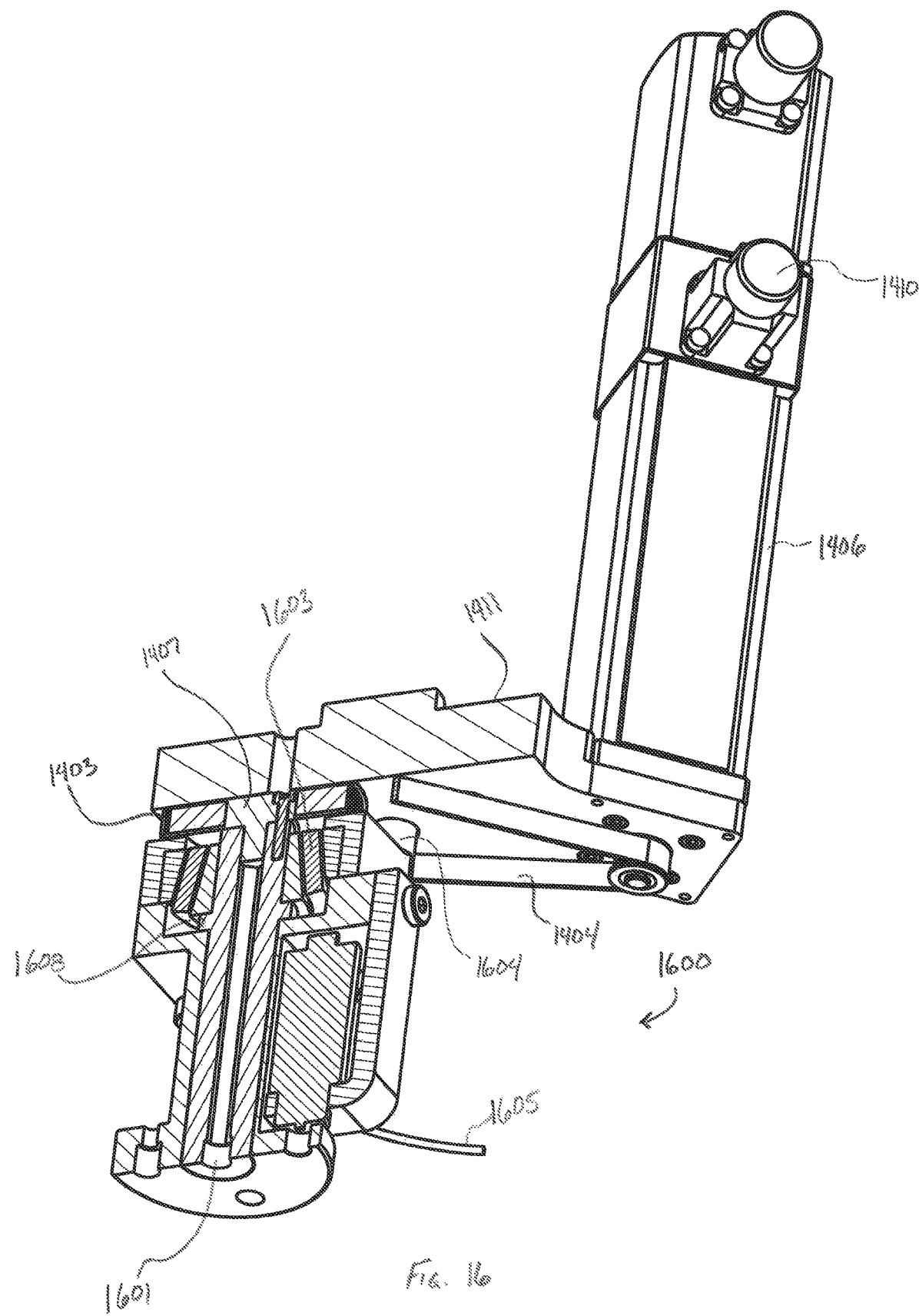
FIG. 16 is a partial cross-section of the instrument holder receiver shown in FIG. 15.

With reference to FIGS. 15 and 16, internal components of the instrument holder receiver 1600 can be arranged as generally described in connection with the receiver 600 of FIG. 6. Due to the hexagonal shape of the male prong 1407, however, a key such as key 607 in FIG. 6, is not required.

As with the receiver 600, the instrument holder receiver 1600 can include a conical bearing 1603 to transmit thrust and side load, a collar 1608 to transmit thrust to the conical bearing 1603, and a wire 1605 for neuromonitoring. Support shafts 1604 are secured to the base plate 1401 at apertures 1405 to support the instrument holder receiver 1600. Other methods to transmit the rotation and torque from second driven wheel 1403 to an instrument holder receiver 1600, and hence an instrument holder 300, and an instrument 207, will present themselves to one of ordinary skill and can be used in accordance with the presently disclosed subject matter.

In operation, the second motor 1406, such as a servomotor, in communication with a controller (not shown), provides a rotational force to rotate second drive wheel 1402. Rotation of drive wheel 1402 initiates the second endless belt 1404 to rotate the second driven wheel 1403, which in turn rotates male prong 1407 and locator pins 1416 to impart rotary action and torque to driveshaft 1601, as best shown in FIG. 16.

As shown in FIGS. 14 and 15, there is one central axis, 1119, for back section 1100 that axially extends from the center of shaft 1103 (see, e.g., FIG. 10). There is a second axis, 1309, for front section 1400 that axially extends from center of male prong 1407 in FIG. 14 and the center of driveshaft 1601, that is offset from, but generally parallel to, central axis 1119. This is distinct from other embodiments, such as disclosed in FIGS. 5-9, in which there is one central axis for both back section 902 and front section 901 that axially extends from the center of load mounting point 903, which is aligned with the center of servomotor shaft 602 (see, e.g., FIGS. 6 and 9).

Figure 18:
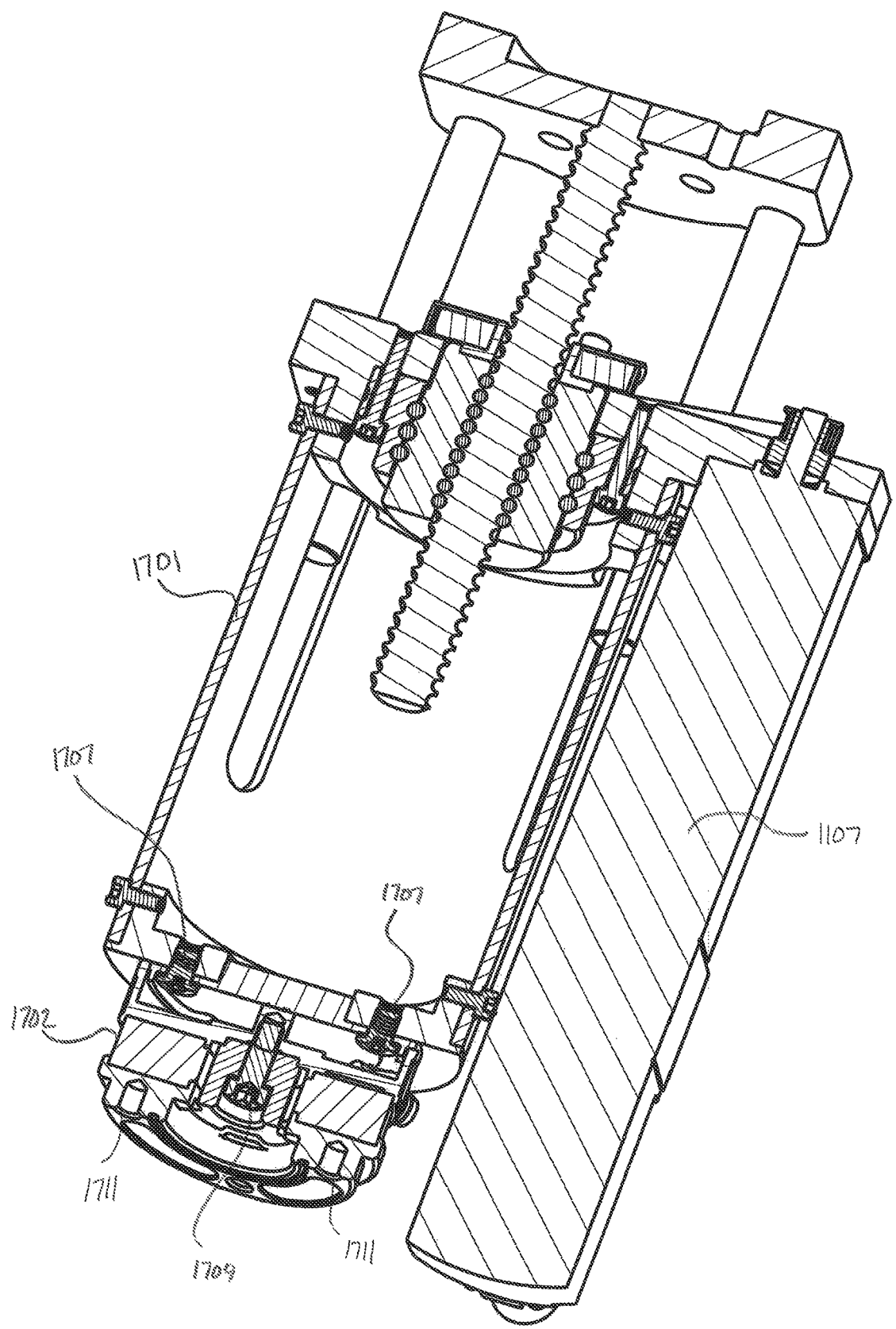
FIG. 18 depicts a cross-section of FIG. 17.

FIGS. 17 and 18 provide an exemplary embodiment of a transducer pedestal system 1700, which joins back section 1100 and front section 1400. A pedestal 1701 is provided to provide enough space for the instrument holder receiver 1600 to operate clear of the motors 1107 and 1406. The pedestal is provided with holes 1703 to provide clearance for the smooth shafts 1116 as the back section 1100 moves the end effector in an axial direction (i.e., "up" as oriented in FIG. 17).

A transducer 1702 is provided that, in this particular embodiment, is engaged with the distal end of the pedestal 1701 via screws 1707. The transducer 1702 includes four female recesses 1711, a center recess 1709, a locator recess 1713, and slots 1715, one or more of which can form the load mounting points for the front or second section 1400, in a similar fashion to load mounting point 903 discussed above in connection with FIG. 9. The transducer 1702 measures multiaxial and rotational force, converts the measured force to a voltage output, with benefit of the control system 2000 described generally in FIG. 20, to provide control based on the measured force and applied voltage.

Figure 19:
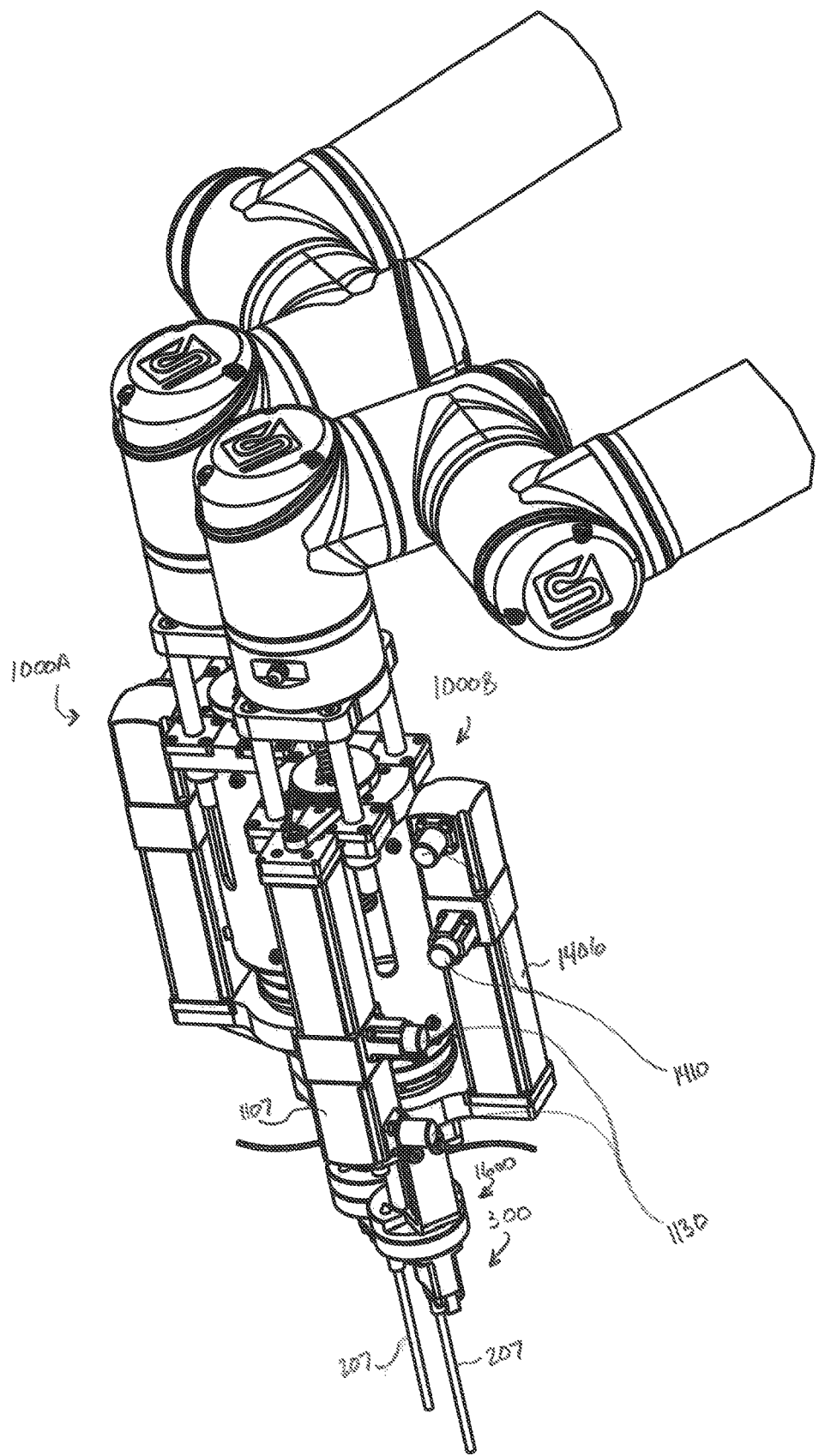
FIG. 19 depicts two end effectors shown to illustrate that all wire connections exit on the same side of the end connector

FIG. 19 depicts two end effectors 1000A and 1000B according to the embodiment depicted in FIGS. 10-18 operating in tandem. Advantages provided by the embodiment disclosed in FIGS. 10-19 will become readily apparent. For example, due to the offset axis 1309 of front section 1300, the instrument holder receivers 600, 1600 for the instrument holder 300, and the instruments 207 themselves can be operated in much closer proximity, as compared to, for example, the embodiment shown in FIGS. 1-9.

As best shown in FIGS. 15 and 19, provision of an offset axis for the front section 1400 allows for ports 1130 for wiring and other inputs associated with the motor 1107 and ports 1410 for wiring and other inputs associated with the second motor 1406 to be conveniently channeled in one general location, on the side of the end effector and generally disposed away from the offset operating area of the instruments 207. As shown in FIG. 15, the instrument holder receiver 1600 is offset from central axis 1119 in a first direction 1417. The motor 1107 includes a housing 1121 that includes ports 1130 for receiving inputs. The inputs (e.g., wires, not shown) exit the ports 1130 in a second direction 1418 generally opposite the first direction 1417.

The programming language of the industrial robot controller may be used to generate a computer code (software) that a robotic surgery system uses to perform surgery. The industrial robot controller and software may coordinate the actions of and feedback from the end effector through a system of electronics designed for this purpose. The end effector described herein may have several electrical inputs and outputs that may be translated to and from inputs and outputs of the industrial robot controller. Part of the end effector system may be a configuration of the electronics for performing this translation.

The inputs and outputs from the electronics on the end effector system may be carried through several different connection types and cable types. Servomotors may typically have one multipin connection for power and one for control and feedback. Transducers may typically use a multi-pin connection. Uni-directional solenoids may typically have one wire to deliver power to energize the device. The neuromonitoring probe may also have a single lead through which current flows when electrical contact is made when a probe gets too close to a neural structure. Cables for all of these connections may be routed from the end effector, along the outside of the robot in a way that does not interfere with its motion, and to the integrated end effector control system. A panel facing the outside of the enclosure for the system may have connectors mounted to it so the appropriate cables from the end effector may be plugged in to the integrated end effector control system.

The inputs and outputs from the industrial robot system controller may also be delivered to the integrated end effector control system using the appropriate cables. Connectors may be mounted to a second panel on the end effector control system enclosure so that the cables from the industrial robot controller may be plugged into the end effector.

Different connectors for different inputs and outputs may be used on the robot system and end effector connection panels to help ensure that everything is connected correctly when the system is being installed by a user.

The enclosure for the integrated end effector control system may contain all of the required electronics to translate the inputs and outputs from the end effector system. The system may require an independent power supply which may be mounted inside of the enclosure and connected to standard AC current available in an operating room. The power supply may be an uninterruptable power supply (UPS) system to prevent damage to the end effector system or electronics in the case of a power interruption. A cooling system may also be incorporated to keep the electronics from overheating.

The servomotor controller electronics may be a subsystem of the integrated end effector control system. The servomotor controller electronics may be an off-the shelf component mounted within the enclosure. The servomotor controller electronics may receive power from the UPS mounted within the enclosure. The connections for the two servomotors in the end effector may be wired from the servomotor controller electronics to the end effector connection panel. The inputs/output from the servomotor controller electronics, which connect back to the robot control computer system, may be wired to the robot system connection panel. The connections from the servomotor controller electronics to the robot control computer system may be standard since many servomotor controllers are designed to be integrated into industrial automation systems.

The interface module for the multiaxial transducer may also be a sub-system of the integrated end effector control system. The interface module may be an off-the shelf component mounted within the enclosure. The interface module may receive power from the internally mounted UPS also. The input and output from the transducer may come from the end effector control panel. The output to the robot system controller computer may go out through the robot control connection panel.

The neuromonitoring electronics module may be a sub-system of the integrated end effector control system. The module may provide stimulating current for the neuromonitoring and detect current passed from the end of the instrument through the patient to the neuromonitoring skin pad. This signal may be conditioned and transmitted to the robot system controller computer. Power for the neuromonitoring electronics module may be provided by the internally mounted UPS.

The solenoid signal converter may relay a binary signal transmitted from the robot system controller computer to either open the latch to release the clamped instrument or allow the latch to return to the closed position to clamp the instrument. The solenoid signal converter may generate a current to energize the latch releasing solenoid when the binary signal is received. This may be necessary since voltage and current from the binary signal may not be enough to energize the solenoid.

Figure 20:
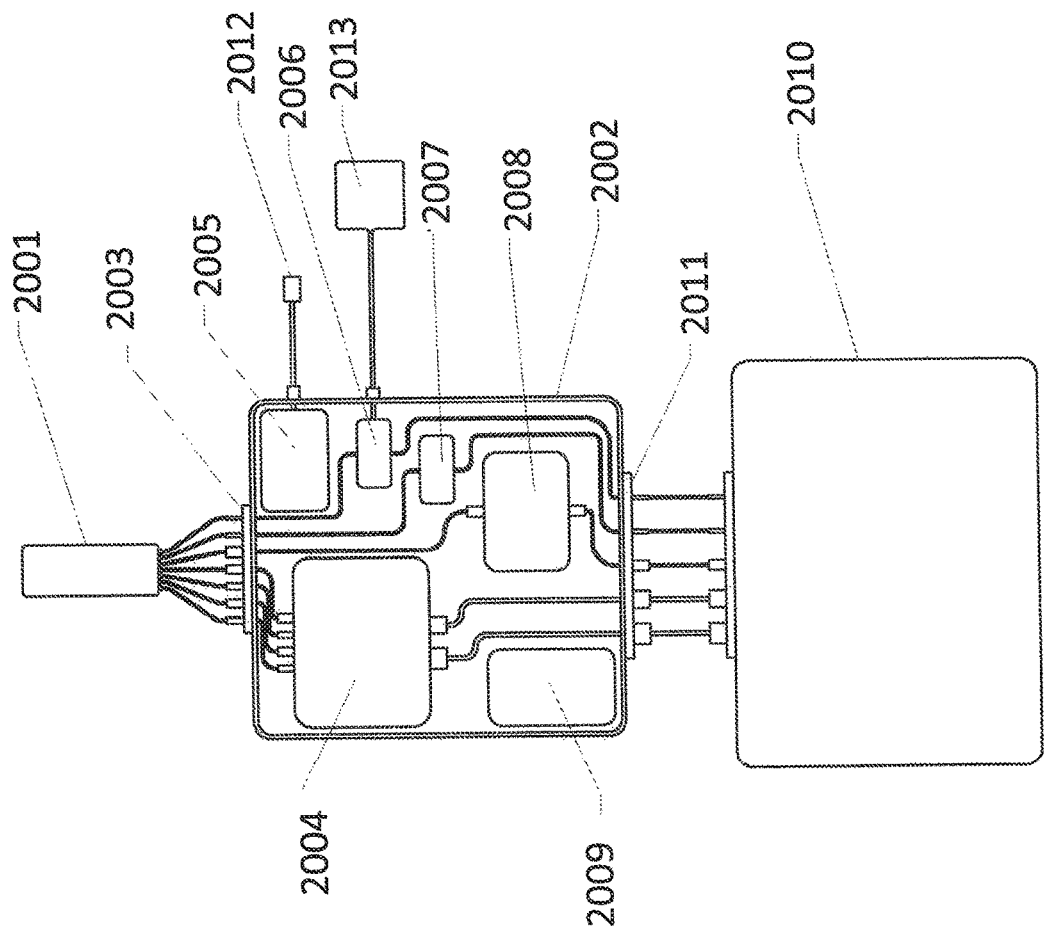
FIG. 20 is an example of an integrated end effector control system interfacing with the end effector and the industrial robotics system.

FIG. 20 is an example of an integrated end effector control system interfacing with the end effector and the industrial robotics system. The end effector 2001 may be connected to the integrated end effector control system enclosure 2002 via an end effector connection panel 2003. The integrated end effector control system enclosure 2002 may include a solenoid motor controller module 2004, a UPS 2005, a neuromonitoring electronics module 2006, a solenoid signal converter 2007, a transducer interface 2008, and a cooling system 2009. The integrated end effector control system is connected to the robot system controller computer 2010 via a robot control connection panel 2011. The UPS 2005 may be connected to the AC power 2012. The neuromonitoring electronics module 2006 may be connected to a neuromonitoring skin pad 2013.

Many different tools may be attached to the instrument holder. For example, some of the tools used may be a wire inserter, a tap, a headless screwdriver, a tulip popper, a cap inserter, a cap torque driver/counter torque, a vision system (for example, a camera) and the like. Additionally, the end effector may be capable of reading an RF signal from a smart implant.

K-wire management may be described herein. The K-wire management may include a nitinol wire that is deployed in a spiral helix shape. The K-wire may be forced to a straight shape within an internal cannula. A K-wire may also be pre-loaded into a headless cannulated screw driver. The K-wire may be put into place with the use of two robots. The first robot may include the use of the end effector described herein. The first robot holds the K-wire while the second robot uses a K-wire gripper to hold the K-wire in a fixed position.

After K-wire insertion, the wire may be held in a fixed position relative to the vertebral body, with the end effector moving pedicle preparation tools axially along the wire. The end effector wire holder and K-wire are designed to prevent the wire from being "pushed along" with the pedicle preparation tool. In contrast, 'pushing along" wire may cause the wire to penetrate too far, potentially resulting in serious injury for a patient.

For a cap inserter tool, two robots may be used. The first robot may include the end effector described herein. The first robot uses the cap inserter tool to insert the cap into a previously placed pedicle screw tulip, while the second robot bends and inserts a rod through the inserted tulip and cap. The first robot may then use the cap inserter tool to tighten the cap, locking the rod into the pedicle screw tulip.

For the headless screwdriver tool, the screw a simply snaps-on and locks in place for insertion. A guide wire may already be preloaded along with a pedicle screw. The guide wire may be a NITINOL material. The guide wire may be loaded into a headless screw driver straitened (under tension). However, once the guide wire is deployed, the end relaxed into a pigtail or helical spiral shape.

A dynamometer may be inserted between the headless screwdriver and the power drill to measure the (maximum) torque applied when inserting the screw. The dynamometer may also be used to limit the amount of torque applied for safety reasons. Torque may also be measured using the load (amps) drawn by the drill motor. A shunt may be placed between the battery and the power drill with resistance that provides for a standard 4-20 mA current as measure across the shunt. A data acquisition device and software may be used to record data and calibrate from current (mA) to torque (Nm).

The end effector may be capable of driving a screw by itself using an automatic screwdriver. For an automatic screwdriver, a stepper motor may count revolutions once the screwdriver begins driving. A screw may be driven in very controlled increments. Data from the recorded torque aids in sizing a motor required for the automatic screwdriver.

A head popper may be used to insert a tulip onto a screw, to guide a rod into place, for verifying the seating of a rod, assembling a locking cap, removing a locking cap, and the like.

A vision system may verify hardware, for example, length, diameter, size, and the like. The vision system may be used for positioning and alignment of implants and the like. The vision system may be part of the industrial robot control package or a standalone system. The vision system may include shape recognition software.

In an exemplary embodiment according to the present invention, data may be provided to the system, stored by the system and provided by the system to users of the system across local area networks (LANs) (e.g., office networks, home networks) or wide area networks (WANs) (e.g., the Internet). In accordance with the previous embodiment, the system may be comprised of numerous servers communicatively connected across one or more LANs and/or WANs. One of ordinary skill in the art would appreciate that there are numerous manners in which the system could be configured and embodiments of the present invention are contemplated for use with any configuration.

In general, the system and methods provided herein may be consumed by a user of a computing device whether connected to a network or not. According to an embodiment of the present invention, some of the applications of the present invention may not be accessible when not connected to a network; however a user may be able to compose data offline that will be consumed by the system when the user is later connected to a network.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature and not restrictive.

The invention claimed is:

1. An end effector of a robotic surgery system comprising:
a fixed plate for attaching an end of a robotic arm;
a shaft extending from the fixed plate;
a sliding plate moveable relative to the fixed plate along an axial direction of the shaft;
a hub assembly mounted to the sliding plate and operatively engaged with the shaft, the hub assembly including:
an idler hub, and
an inner bearing moveable relative to the idler hub and operatively engaged with the shaft, whereby rotation of the inner bearing moves the sliding plate along the axial direction of the shaft; and
a pulley that includes a driven wheel connected to the inner bearing, whereby rotation of the driven wheel drives rotation of the inner bearing.

2. The end effector of claim 1, wherein the idler hub circumscribes the inner bearing.

3. The end effector of claim 1, wherein the idler hub is directly mounted to the sliding plate.

4. The end effector of claim 1, wherein the hub assembly includes thrust bearings between the idler hub and inner bearing.

5. The end effector of claim 1, wherein the pulley further comprises:
a drive wheel laterally spaced from the driven wheel;
an endless belt extending between the drive wheel and driven wheel; and
a motor operatively engaged with the drive wheel to drive rotation thereof.

6. The end effector of claim 1, wherein the pulley has a speed ratio of at least 2:1.

7. The end effector of claim 1, wherein the axial direction of the shaft transverses a major plane of the fixed plate.

8. The end effector of claim 1, further comprising:
a base plate attached to the sliding plate;
an instrument holder receiver; and
a second pulley secured to the base plate and operatively engaged with the instrument holder receiver for imparting a rotary action to the instrument holder receiver.

9. The end effector of claim 8, wherein the second pulley comprises:
a second driven wheel operatively engaged with the instrument holder receiver;
a second drive wheel laterally offset from the second driven wheel;
a second endless belt extending between the second driven wheel and the second drive wheel; and
a second motor operatively engaged with the second drive wheel to drive rotation thereof.

10. The end effector of claim 9, wherein a rotational axis of the second driven wheel is laterally offset from the axial direction of the shaft.

11. The end effector of claim 8, further comprising a pedestal connected to the base plate and the sliding plate.

12. The end effector of claim 11, further comprising a transducer secured to the base plate and the pedestal.

13. The end effector of claim 11, wherein the motor and the second motor are disposed about a lateral periphery of the pedestal.

14. The end effector of claim 1, wherein the motor is housed within a housing having ports about a lateral side of the housing for receiving inputs.

15. An end effector of a robotic surgery system comprising:
a fixed plate for attaching to a distal end of a robotic arm;
a shaft extending from a central location of the fixed plate;
a sliding plate moveable relative to the first plate in an axial direction of the shaft;
a first pulley operatively engaged with the sliding plate;
a first motor operatively engaged with the first pulley;
a base plate attached to the sliding plate;
an instrument holder receiver positioned offset from the shaft; and
a second pulley secured to the base plate and operatively engaged with the instrument holder receiver.

16. The end effector of claim 15, further comprising a second motor operatively engaged with the second pulley and laterally offset from the instrument holder receiver.

17. The end effector of claim 15, further comprising:
a pedestal coaxial to the shaft and disposed between the sliding plate and the base plate; and a transducer secured to the pedestal and the base plate.

18. The end effector of claim 17, wherein the first motor and the second motor are disposed about a lateral periphery of the pedestal.

19. The end effector of claim 18, wherein the instrument holder receiver is offset from the shaft in a first direction, and the first motor comprises a housing having ports about a lateral side of the housing for receiving inputs, said ports facing a direction generally opposite the first direction.

20. A robotic surgery system comprising at least two robotic arms operating in tandem, the at least two robotic arms each having the end effector according to claim 15.

* * * * *